(12) United States Patent
Jorand-Lebrun et al.

(10) Patent No.: US 9,975,902 B2
(45) Date of Patent: May 22, 2018

(54) COMPOUNDS FOR THE INHIBITION OF CYCLOPHILINS AND USES THEREOF

(71) Applicant: Merck Patent GmbH, Darmstadt (DE)

(72) Inventors: Catherine Jorand-Lebrun, Arlington, MA (US); Theresa L. Johnson, Salem, MA (US); Ulrich Graedler, Weinheim (DE); Xuliang Jiang, Braintree, MA (US); Santosh Kulkarni, Bangalore (IN)

(73) Assignee: Merck Patent GmbH, Darmstadt (DE)

( * ) Notice: Subject to any disclaimer, the term of this patent is extended or adjusted under 35 U.S.C. 154(b) by 0 days. days.

(21) Appl. No.: 15/474,193

(22) Filed: Mar. 30, 2017

(65) Prior Publication Data
US 2017/0283427 A1    Oct. 5, 2017

Related U.S. Application Data

(60) Provisional application No. 62/315,890, filed on Mar. 31, 2016.

(51) Int. Cl.
| | |
|---|---|
| *C07D 491/18* | (2006.01) |
| *C07D 209/48* | (2006.01) |
| *C07D 209/70* | (2006.01) |
| *C07D 491/08* | (2006.01) |
| *C07D 401/12* | (2006.01) |
| *C07D 403/12* | (2006.01) |

(52) U.S. Cl.
CPC ......... *C07D 491/18* (2013.01); *C07D 209/48* (2013.01); *C07D 209/70* (2013.01); *C07D 401/12* (2013.01); *C07D 403/12* (2013.01); *C07D 491/08* (2013.01)

(58) Field of Classification Search
CPC ... C07D 491/18; C07D 209/48; C07D 209/70
See application file for complete search history.

(56) References Cited

FOREIGN PATENT DOCUMENTS

| FR | 2 860 793 A1 | | 4/2005 |
|---|---|---|---|
| WO | WO2005037839 | * | 4/2005 |
| WO | 2011/076784 A2 | | 6/2011 |

OTHER PUBLICATIONS

Daum, 2009, Biochemistry, vol. 48, No. 26, p. 6268-6277.*
STN Reg. No. 1287480-22-1, entered into Registry Apr. 29, 2011.*
STN Reg. No. 1287480-22-11287467-01-9, entered into Registry Apr. 29, 2011.*
STN Reg. No. 1287466-94-7, entered into Registry Apr. 29, 2011.*
STN Reg. No. 1009546-68-2, entered into Registry Mar. 21, 2008.*
STN Reg. No. 1008185-63-4, entered into Registry Mar. 16, 2008.*
STN Reg. No. 1589790-72-6, entered into STN Apr. 24, 2014 (Year: 2014).*
Berge et al., S.M. J. Pharmaceutical Sciences, 1977, 66, 1-19.
Database Registry, Chemical Abstracts Service, Columbus Ohio, US; Apr. 29, 2011, XP002770589, Database accession No. 1287476-94-7.
Database Registry, Chemical Abstracts Service, Columbus Ohio, US; Apr. 24, 2014, XP002770590, Database accession No. 1589491-43-9.
Database Registry, Chemical Abstracts Service, Columbus Ohio, US; Jan. 12, 2011, XP002770591, Database accession No. 1259151-83-1.
Database Registry, Chemical Abstracts Service, Columbus Ohio, US; Dec. 27, 2015, XP002770592, Database accession No. 1837101-05-9.
Database Registry, Chemical Abstracts Service, Columbus Ohio, US; Apr. 29, 2011, XP002770593, Database accession No. 1287433-36-6.
Database Registry, Chemical Abstracts Service, Columbus Ohio, US; Apr. 17, 2011, XP002770594, Database accession No. 1280871-46-6.
Database Registry, Chemical Abstracts Service, Columbus Ohio, US; Jan. 12, 2011, XP002770595, Database accession No. 1259041-31-0.
Database Registry, Chemical Abstracts Service, Columbus Ohio, US; Dec. 18, 2007, XP002770596, Database accession No. 958593-22-1.
Foster, Adv. Drug Res. 14, 1-40, 1985.
Gillette et al, Biochemistry 33(10) 2927-2937, 1994.
Flanzlik et al., J. Org. Chem. 55, 3992-3997, 1990.
International Search Report, dated Jun. 14, 2017.
Jarman et al. Carcinogenesis 16(4), 683-688, 1993.
Ni, Shuaishuai, et al., Discovering Potent Small Molecule Inhibitors of Cyclophilin A Using de Novo Drug Design Approach, Journal of Medicinal Chemistry, vol. 52, No. 17, Sep. 10, 2009.
Pang, Xiaodong et al., Discovery of a potent peptidic cyclophilin A inhibitor Trp-Gly-Pro, European Journal of Medicinal Chemistry, Editions Scientifique Elsevier, Paris FR, vol. 46, No. 5, Feb. 12, 2011, pp. 1701-1705.
Periodic Table of the Elements, CAS version, Handbook of Chemistry and Physics, 75th Ed.
Reider et al., J. Org. Chem. 52, 3326-3334, 1987.
Smith, M.B. and March, J., Ed: , March's Advanced Organic Chemistry, 5th Ed, John Wiley & Sons, New York: 2001.
Sorrell, Thomas, "Organic Chemistry", University Science Books, Sausalito: 1999.

* cited by examiner

*Primary Examiner* — Rebecca L Anderson
*Assistant Examiner* — Karen Cheng
(74) *Attorney, Agent, or Firm* — Dwight D. Kim; EMD Serono Research and Development Institute

(57) ABSTRACT

The present invention relates to compounds, and pharmaceutically acceptable compositions thereof, useful as inhibitors of cyclophilins, and for the treatment of cyclophilin-related disorders.

15 Claims, No Drawings

COMPOUNDS FOR THE INHIBITION OF CYCLOPHILINS AND USES THEREOF

RELATED APPLICATIONS

This application claims the benefit of U.S. Provisional application No. 62/315,890, filed on Mar. 31, 2016, the content of which is incorporated in its entirety by reference.

TECHNICAL FIELD OF THE INVENTION

The present invention relates to dioxo-hexahydroisoindolyl compounds useful as inhibitors of Cyclophilins. The invention also provides pharmaceutically acceptable compositions comprising compounds of the present invention and methods of using said compositions in the treatment of various disorders.

BACKGROUND OF THE INVENTION

Cyclophilins or peptidyl-prolyl isomereases (PPAses) are widely expressed enzymes which catalyse the conversion of proline residues peptide bonds from trans to cis conformation. They play a critical role in important cellular processes and have been proposed as potential targets for the treatment of a number of diseases such as viral infections, inflammation, neurologic disorders, cardiac failure and cancer.

SUMMARY OF THE INVENTION

It has now been found that compounds of this invention, and pharmaceutically acceptable compositions thereof, are effective as inhibitors of cyclophilins. Such compounds have general formula I:

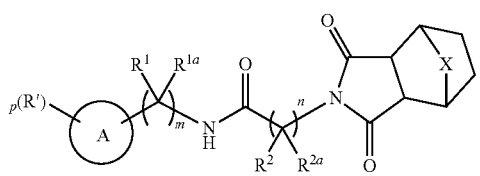

I or a pharmaceutically acceptable salt thereof, wherein each of Ring A, X, R', $R^1$, $R^{1a}$, $R^2$, $R^{2a}$, m, n, and p, is as defined and described in embodiments herein.

Compounds of the present invention, and pharmaceutically acceptable compositions thereof, are useful for treating a variety of diseases, disorders or conditions, associated with cyclophilin activity. Such diseases, disorders, or conditions include those described herein.

DETAILED DESCRIPTION OF CERTAIN EMBODIMENTS

1. General Description of Compounds of the Invention

In certain embodiments, the present invention provides inhibitors of cyclophilins. In some embodiments, such compounds include those of the formulae described herein, or a pharmaceutically acceptable salt thereof, wherein each variable is as defined and described herein.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_7$ hydrocarbon that is completely saturated or that contains one or more units of unsaturation, but which is not aromatic, that has a single point of attachment to the rest of the molecule. Exemplary aliphatic groups are linear or branched, substituted or unsubstituted $C_1$-$C_8$ alkyl, $C_2$-$C_8$ alkenyl, $C_2$-$C_8$ alkynyl groups and hybrids thereof such as (cycloalkyl)alkyl, (cycloalkenyl) alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, or phosphorus (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group. The term "alkynylene" refers to a bivalent alkynyl group. A substituted alkynylene chain is a group containing at least one triple bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" is used interchangeably with the term "aryl ring". In certain embodiments of the present invention, "aryl" refers to an aromatic ring system. Exemplary aryl groups are phenyl, biphenyl, naphthyl, anthracyl and the like, which optionally includes one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 r electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group is optionally mono- or bicyclic. The term "heteroaryl" is used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen is N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydropyranyl, tetrahydrothiophenyl pyrrolidinyl, piperidinyl, pyrrolinyl, morpholinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, certain compounds of the invention contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure (e.g.,

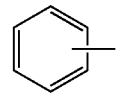

refers to at least

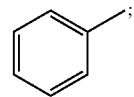

and

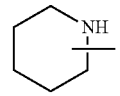

refers to at least

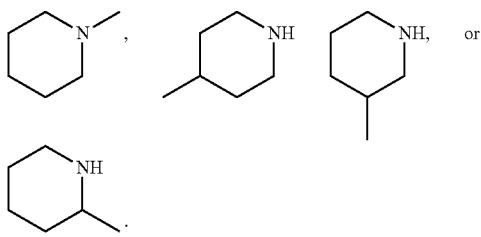

Unless otherwise indicated, an "optionally substituted" group has a suitable substituent at each substitutable position of the group, and when more than one position in any given structure is substituted with more than one substituent selected from a specified group, the substituent is either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium; halogen; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$C(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which are optionally substituted with R$^\circ$; —(CH$_2$)$_{0-4}$O(CH$_2$)$_{0-1}$Ph which is optionally substituted with R$^\circ$; —CH=CHPh, which is optionally substituted with R$^\circ$; —(CH$_2$)$_{0-4}$O(CH$_2$)$_{0-1}$-pyridyl which is optionally substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ$$_2$; —N(R$^\circ$)C(S)NR$^\circ$$_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ$$_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ$$_3$; —(CH$_2$)$_{0-4}$OC(O)R$^\circ$; —OC(O)(CH$_2$)$_{0-4}$SR$^\circ$, SC(S)SR$^\circ$; —(CH$_2$)$_{0-4}$SC(O)R$^\circ$; —(CH$_2$)$_{0-4}$C(O)NR$^\circ$$_2$; —C(S)NR$^\circ$$_2$; —C(S)SR$^\circ$; —SC(S)SR$^\circ$, —(CH$_2$)$_{0-4}$OC(O)NR$^\circ$$_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ$$_2$; —(CH$_2$)$_{0-4}$S(O)R$^\circ$; —N(R$^\circ$)S(O)$_2$NR$^\circ$$_2$; —N(R$^\circ$)S(O)$_2$R$^\circ$; —N(OR$^\circ$)R$^\circ$; —C(NH)NR$^\circ$$_2$; —P(O)$_2$R$^\circ$; —P(O)R$^\circ$$_2$; —OP(O)R$^\circ$$_2$; —OP(O)(OR$^\circ$)$_2$; SiR$^\circ$$_3$; —(C$_{1-4}$ straight or branched alkylene)O—N(R$^\circ$)$_2$; or —(C$_{1-4}$ straight or branched)alkylene)C(O)O—N(R$^\circ$2, wherein each R$^\circ$ is optionally substituted as defined below and is independently hydrogen, C$_{1-6}$ aliphatic, —CH$_2$Ph, —O(CH$_2$)$_{0-1}$Ph, —NH(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which is optionally substituted as defined below.

Suitable monovalent substituents on R$^\circ$ (or the ring formed by taking two independent occurrences of R$^\circ$ together with their intervening atoms), are independently deuterium, halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\bullet$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which is substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which is optionally substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

In certain embodiments, the terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

- —F, —Cl, —Br, —I, deuterium,
- —OH, protected hydroxy, alkoxy, oxo, thiooxo,
- —NO₂, —CN, CF₃, N₃,
- —NH₂, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino,
- —O— alkyl, —O— alkenyl, —O— alkynyl, —O— cycloalkyl, —O-aryl, —O-heteroaryl, —O-heterocyclic,
- —C(O)— alkyl, —C(O)— alkenyl, —C(O)— alkynyl, —C(O)— carbocyclyl, —C(O)-aryl, —C(O)— heteroaryl, —C(O)-heterocyclyl,
- —CONH₂, —CONH— alkyl, —CONH— alkenyl, —CONH— alkynyl, —CONH-carbocyclyl, —CONH-aryl, —CONH-heteroaryl, —CONH-heterocyclyl,
- —OCO₂— alkyl, —OCO₂— alkenyl, —OCO₂— alkynyl, —OCO₂— carbocyclyl, —OCO₂-aryl, —OCO₂-heteroaryl, —OCO₂-heterocyclyl, —OCONH₂, —OCONH— alkyl, —OCONH— alkenyl, —OCONH— alkynyl, —OCONH— carbocyclyl, —OCONH-aryl, —OCONH— heteroaryl, —OCONH— heterocyclyl,
- —NHC(O)— alkyl, —NHC(O)— alkenyl, —NHC(O)— alkynyl, —NHC(O)— carbocyclyl, —NHC(O)-aryl, —NHC(O)-heteroaryl, —NHC(O)-heterocyclyl, —NHCO₂— alkyl, —NHCO₂— alkenyl, —NHCO₂— alkynyl, —NHCO₂— carbocyclyl, —NHCO₂— aryl, —NHCO₂— heteroaryl, —NHCO₂-heterocyclyl, —NHC(O)NH₂, —NHC(O)NH— alkyl, —NHC(O)NH— alkenyl, —NHC(O)NH— alkynyl, —NHC(O)NH— carbocyclyl, —NHC(O)NH-aryl, —NHC(O)NH-heteroaryl, —NHC(O)NH— heterocyclyl, NHC(S)NH₂, —NHC(S)NH— alkyl, —NHC(S)NH— alkenyl, —NHC(S)NH— alkynyl, —NHC(S)NH— carbocyclyl, —NHC(S)NH— aryl, —NHC(S)NH-heteroaryl, —NHC(S)NH-heterocyclyl, —NHC(NH)NH₂, —NHC(NH)NH— alkyl, —NHC(NH)NH-alkenyl, —NHC(NH)NH— alkynyl, —NHC(NH)NH— carbocyclyl, —NHC(NH)NH-aryl, —NHC(NH)NH-heteroaryl, —NHC(NH)NH— heterocyclyl, —NHC(NH)— alkyl, —NHC(NH)— alkenyl, —NHC(NH)— alkenyl, —NHC(NH)— carbocyclyl, —NHC(NH)-aryl, —NHC(NH)-heteroaryl, —NHC(NH)-heterocyclyl,
- —C(NH)NH— alkyl, —C(NH)NH— alkenyl, —C(NH)NH— alkynyl, —C(NH)NH— carbocyclyl, —C(NH)NH-aryl, —C(NH)NH-heteroaryl, —C(NH)NH-heterocyclyl,
- —S(O)— alkyl, —S(O)— alkenyl, —S(O)— alkynyl, —S(O)— carbocyclyl, —S(O)-aryl, —S(O)-heteroaryl, —S(O)-heterocyclyl —SO₂NH₂, —SO₂NH— alkyl, —SO₂NH— alkenyl, —SO₂NH— alkynyl, —SO₂NH— carbocyclyl, —SO₂NH— aryl, —SO₂NH— heteroaryl, —SO₂NH— heterocyclyl,
- —NHSO₂— alkyl, —NHSO₂— alkenyl, —NHSO₂— alkynyl, —NHSO₂— carbocyclyl, —NHSO₂-aryl, —NHSO₂-heteroaryl, —NHSO₂-heterocyclyl,
- —CH₂NH₂, —CH₂SO₂CH₃,
- -mono-, di-, or tri-alkyl silyl,
- -alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S— alkyl, —S— alkenyl, —S— alkynyl, —S— carbocyclyl, —S-aryl, —S-heteroaryl, —S-heterocyclyl, or methylthiomethyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N⁺ (C₁₋₄ alkyl)₄ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, tautomers, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C- enriched carbon are within the scope of this invention. In some embodiments, the group comprises one or more deuterium atoms.

There is furthermore intended that a compound of the formula I includes isotope-labeled forms thereof. An isotope-labeled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phos-phorus, fluo-rine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug, thereof or a pharmaceutically acceptable salt of either which contains one or more of the above-mentioned isotopes and/or other isotopes of other atoms is intended to be part of the present invention. An isotope-labeled compound of the formula I can be used in a number of beneficial ways. For example, an isotope-labeled compound of the formula I into which, for example, a radioisotope, such as $^3H$ or $^{14}C$, has been incorporated, is suitable for medicament and/or substrate tissue distribution assays. These radioisotopes, i.e. tritium ($^3H$) and carbon-14 ($^{14}C$), are particularly preferred owing to simple preparation and excellent detectability. Incorporation of heavier isotopes, for example deuterium ($^2H$), into a compound of the formula I has therapeutic advantages owing to the higher metabolic stability of this isotope-labeled compound. Higher metabolic stability translates directly into an increased in vivo half-life or lower dosages, which under most circumstances would represent a preferred embodiment of the present invention. An isotope-labeled compound of the formula I can usually be prepared by carrying out the procedures disclosed in the synthesis schemes and the related description, in the example part and in the preparation part in the present text, replacing a non-isotope-labeled reactant by a readily available isotope-labeled reactant. Compounds of the invention may be substituted by $^{18}F$, for use as PET imaging agents.

Deuterium ($^2H$) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2-7$ are typical. If this rate difference is successfully applied to a com-pound of the formula I that is susceptible to oxidation, the profile of this compound in vivo can be drastically modified and result in improved pharmacokinetic properties.

When discovering and developing therapeutic agents, the person skilled in the art is able to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concen-tra-tion at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

As used herein, the term "modulator" is defined as a compound that binds to and/or inhibits the target with measurable affinity. In certain embodiments, a modulator has an $IC_{50}$ and/or binding constant of less about 50 μM. In certain embodiments, a modulator has an $IC_{50}$ and/or binding constant of less than about 5 μM. In certain embodiments, a modulator has an $IC_{50}$ and/or binding constant of between about 1 to about 5 μM. In certain embodiments, a modulator has an $IC_{50}$ and/or binding constant of less than about 1 μM. In certain embodiments, a modulator has an $IC_{50}$ and/or binding constant of between about 500 to about 1000 nM. In certain embodiments, a modulator has an $IC_{50}$ and/or binding constant of less than about 500 nM. In certain embodiments, a modulator has an $IC_{50}$ and/or binding constant of between about 100 to about 500 nM. In certain embodiments, a modulator has an $IC_{50}$ and/or binding constant of less than about 100 nM. In certain embodiments, a modulator has an $IC_{50}$ and/or binding constant of between about 10 to about 100 nM. In certain embodiments, a modulator has an $IC_{50}$ and/or binding constant of less than about 10 nM.

The terms "measurable affinity" and "measurably inhibit," as used herein, means a measurable change in cyclophilin activity between a sample comprising a compound of the present invention, or composition thereof, and cyclophilin, and an equivalent sample comprising cyclophilin, in the absence of said compound, or composition thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

3. Description of Exemplary Compounds

According to one aspect, the present invention provides a compound of formula I,

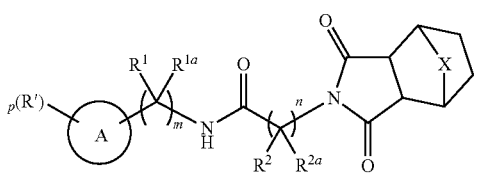

I or a pharmaceutically acceptable salt thereof, wherein:
Ring A is $C_{3-10}$ aryl, which is optionally substituted;
each R' is independently —R, halogen, -haloalkyl, -hydroxyalkyl, —OR, —C(O)R, —$CO_2$R, —C(O)N(R)$_2$, —NRC(O)R, or —N(R)$_2$;
each $R^1$ is independently —H or $C_{1-6}$ aliphatic which is optionally substituted;
each $R^{1a}$ is independently —H or $C_{1-6}$ aliphatic which is optionally substituted;
or $R^1$ and $R^{1a}$ taken together with the atom to which they are attached form a 3-7 membered carbocyclic ring optionally having 1-4 heteroatoms independently selected from nitrogen, oxygen, or sulfur, which is optionally substituted;
each $R^2$ is independently —H or $C_{1-6}$ aliphatic which is optionally substituted;
each $R^{2a}$ is independently —H or $C_{1-6}$ aliphatic which is optionally substituted;
X is $CH_2$ or O; or X and the bonds attached to X are absent;
each R is independently hydrogen, $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or
two R groups on the same atom are taken together with the atom to which they are attached to form a $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
m is 1 or 2;
n is 1 or 2; and
p is 1, 2, 3, 4, or 5.

In certain embodiments, Ring A is phenyl.

In certain embodiments, Ring A is phenyl which is fused with a 5-10 membered saturated or partially unsaturated heterocyclic mono- or bicyclic ring having 1-3 heteroatoms independently selected from nitrogen, oxygen, or sulfur; which is optionally substituted.

In certain embodiments, Ring A is phenyl which is fused with a 7-9 membered saturated or partially unsaturated heterocyclic mono- or bicyclic ring having 1-3 heteroatoms independently selected from nitrogen, oxygen, or sulfur; which is optionally substituted.

In certain embodiments, each R' is independently —R, —OR, —C(O)R, —$CO_2$R, —C(O)N(R)$_2$, —NRC(O)R, or —N(R)$_2$.

In certain embodiments, each R' is independently —R, —OR, or —N(R)$_2$.

In certain embodiments, each R' is independently H, -Me, -Et, —Pr, -iPr, straight chain or branched butyl, straight chain or branched pentyl, or straight chain or branched hexyl, —OR, or —N(R)$_2$.

In certain embodiments, each R' is independently H, -Me, -Et, —OH, or —$NH_2$.

In certain embodiments, Ring A is

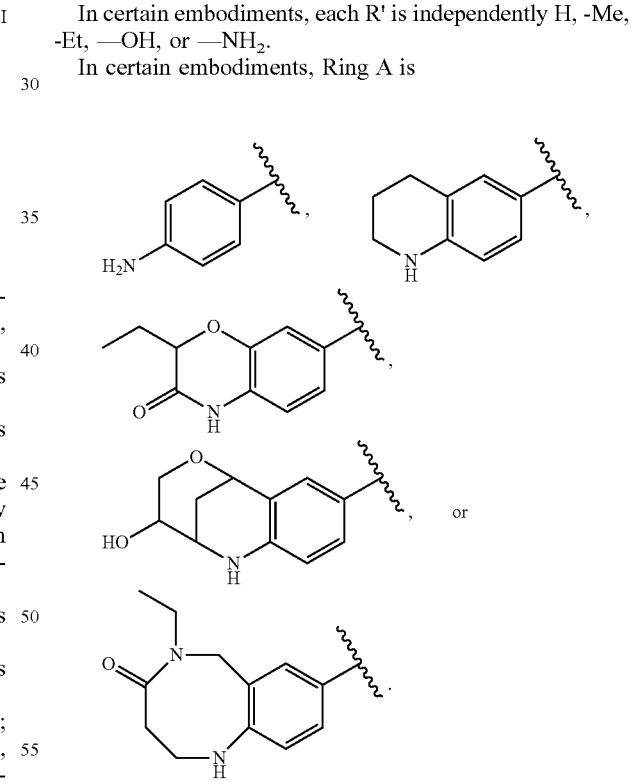

In certain embodiments, Ring A is

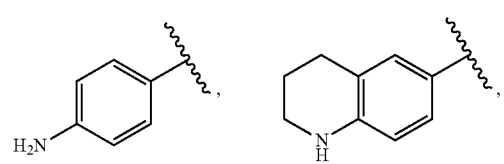

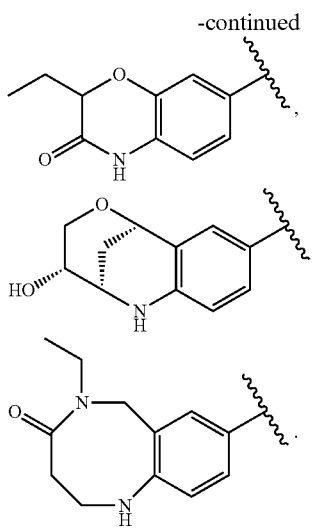

In certain embodiments, each $R^1$ is independently —H.

In certain embodiments, each $R^1$ is independently -Me, -Et, —Pr, -iPr, straight chain or branched -Bu, straight chain or branched penyl, or straight chain or branched hexyl.

In certain embodiments, each $R^1$ is independently -Me.

In certain embodiments, each $R^{1a}$ is independently —H.

In certain embodiments, each $R^{1a}$ is independently -Me, -Et, —Pr, -iPr, straight chain or branched -Bu, straight chain or branched penyl, or straight chain or branched hexyl.

In certain embodiments, $R^1$ and $R^{1a}$ taken together with the atom to which they are attached form a cyclopropyl, cyclobutyl, cyclopentyl, or cyclohexyl, each of which is optionally substituted.

In certain embodiments, $R^1$ and $R^{1a}$ taken together with the atom to which they are attached form a cyclopropyl.

In certain embodiments, each $R^2$ is independently —H.

In certain embodiments, each $R^2$ is independently -Me, -Et, —Pr, -iPr, straight chain or branched -Bu, straight chain or branched penyl, or straight chain or branched hexyl.

In certain embodiments, each $R^{2a}$ is independently —H.

In certain embodiments, each $R^{2a}$ is independently -Me, -Et, —Pr, -iPr, straight chain or branched -Bu, straight chain or branched penyl, or straight chain or branched hexyl.

In certain embodiments, X is $CH_2$.

In certain embodiments, X is O.

In certain embodiments, X, and the bonds attached to X, are absent.

In certain embodiments, the present invention provides a compound of formula II,

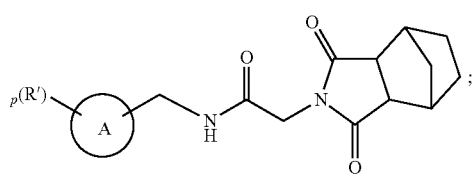

or a pharmaceutically acceptable salt thereof, wherein each of Ring A, R', and p, is as defined above and described in embodiments, classes and subclasses above and herein, singly or in combination.

In certain embodiments, the present invention provides a compound of formula III,

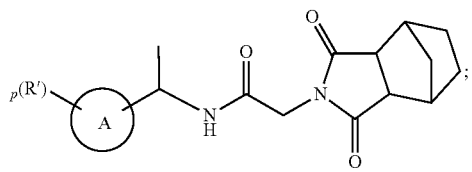

or a pharmaceutically acceptable salt thereof, wherein each of Ring A, R', and p, is as defined above and described in embodiments, classes and subclasses above and herein, singly or in combination.

In certain embodiments, the present invention provides a compound of formula IV:

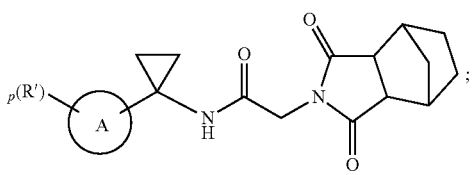

or a pharmaceutically acceptable salt thereof, wherein each of Ring A, R', and p, is as defined above and described in embodiments, classes and subclasses above and herein, singly or in combination.

In certain embodiments, the present invention provides a compound of formula V:

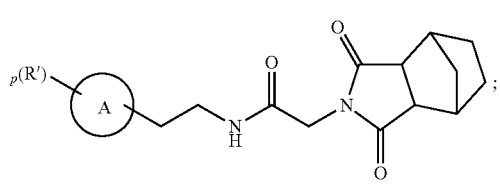

or a pharmaceutically acceptable salt thereof, wherein each of Ring A, R', and p, is as defined above and described in embodiments, classes and subclasses above and herein, singly or in combination.

In certain embodiments, the present invention provides a compound of formula VI,

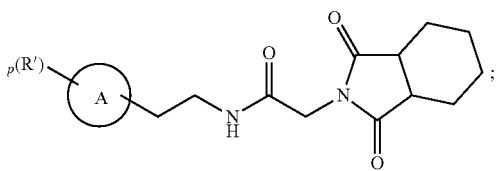

or a pharmaceutically acceptable salt thereof, wherein each of Ring A, R', and p, is as defined above and described in embodiments, classes and subclasses above and herein, singly or in combination.

In certain embodiments, the present invention provides a compound of formula VII,

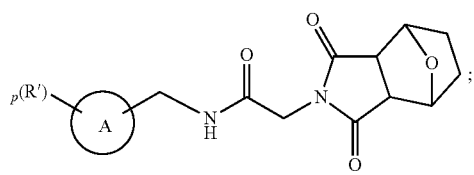

VII or a pharmaceutically acceptable salt thereof, wherein each of Ring A, R', and p, is as defined above and described in embodiments, classes and subclasses above and herein, singly or in combination.

In certain embodiments, the compounds embodied by the invention include racemic structures. In certain embodiments, the compounds embodied by the invention include the (R) enantiomer. In certain embodiments, the compounds embodied by the invention include the (S) enantiomer. In certain embodiments, each enantiomer is over 50% enantiopure. In certain embodiments, each enantiomer is over 75% enantiopure. In certain embodiments, each enantiomer is over 90% enantiopure. In certain embodiments, each enantiomer is over 50% enantiopure. In certain embodiments, each enantiomer is over 95% enantiopure. In certain embodiments, each enantiomer is over 97% enantiopure. In certain embodiments, each enantiomer is over 99% enantiopure.

In certain embodiments, the invention provides a compound of any of the formulae presented herein, wherein each of Ring A, R', $R^1$, $R^{1a}$, $R^2$, $R^{2a}$, R, X, m, n, and p, is as defined above and described in embodiments, classes and subclasses above and herein, singly or in combination.

In certain embodiments, the invention provides a compound selected from Table 1:

TABLE 1

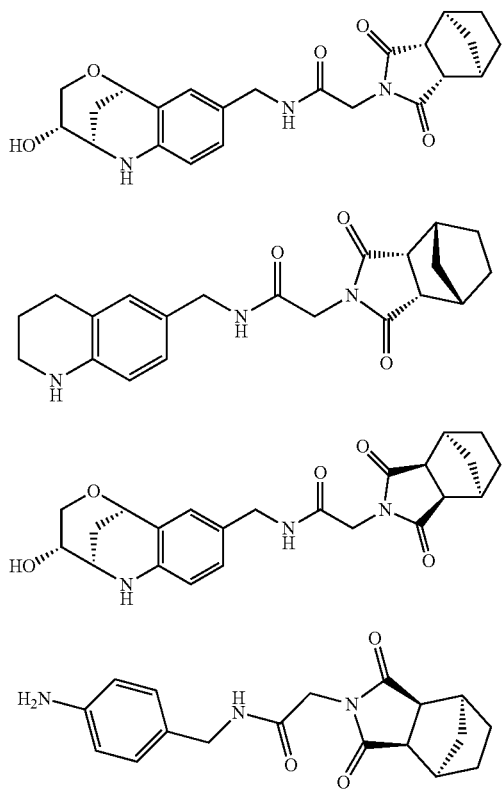

TABLE 1-continued

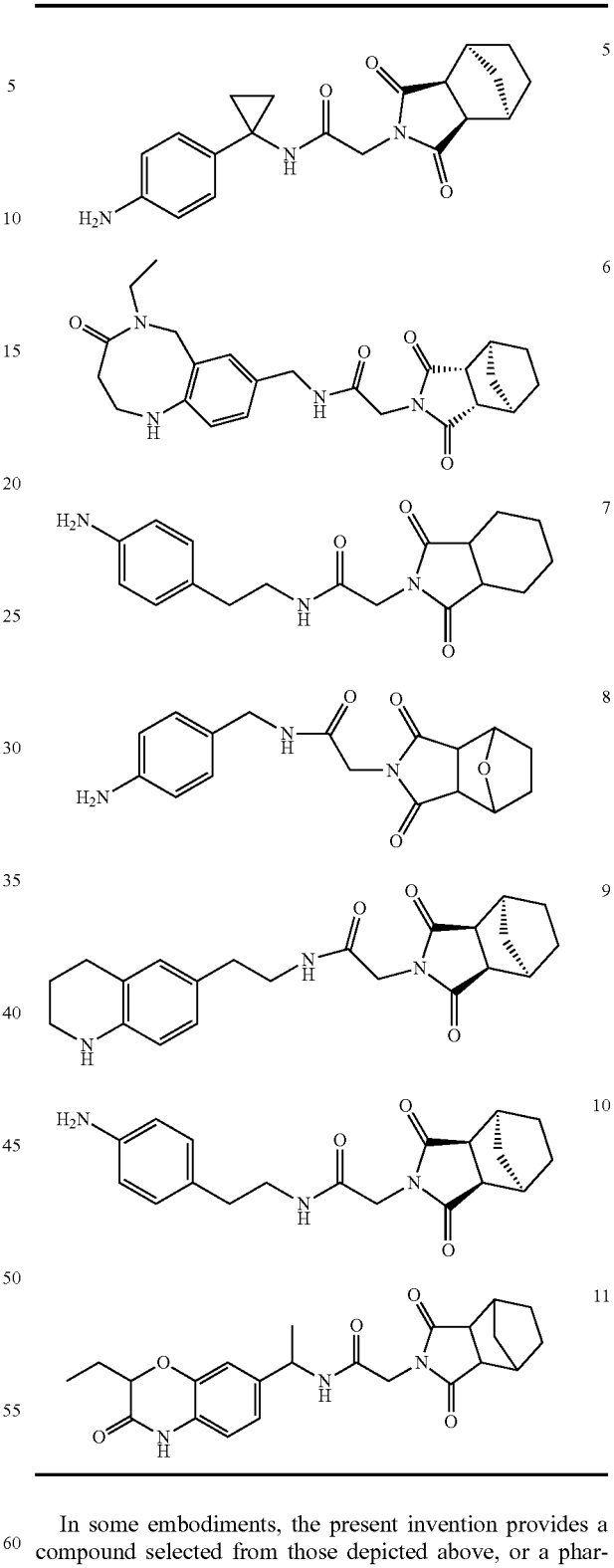

In some embodiments, the present invention provides a compound selected from those depicted above, or a pharmaceutically acceptable salt thereof.

Various structural depictions may show a heteroatom without an attached group, radical, charge, or counterion. Those of ordinary skill in the art are aware that such depictions are meant to indicate that the heteroatom is attached to hydrogen (e.g.,

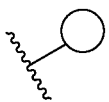

is understood to be

In certain embodiments, the compounds of the invention were synthesized in accordance with Schemes below. More specific examples of compounds made utilizing the Schemes are provided in the Examples below.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit cyclophilins in a biological sample or in a patient. In certain embodiments, the amount of compound in compositions of this invention is such that is effective to measurably inhibit cyclophilins in a biological sample or in a patient. In certain embodiments, a composition of this invention is formulated for administration to a patient in need of such composition.

The term "patient" or "subject", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that are used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention are administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention include aqueous or oleaginous suspension. These suspensions are formulated according to techniques known in the art using suitable dispersing or wetting agents and suspending agents. The sterile injectable preparation is also be a sterile injectable solution or suspension in a non-toxic parenterally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium.

For this purpose, any bland fixed oil employed includes synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms are also be used for the purposes of formulation.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Alternatively, pharmaceutically acceptable compositions of this invention are administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention are also administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches are also used.

For topical applications, provided pharmaceutically acceptable compositions are formulated in a suitable ointment containing the active component suspended or dissolved in one or more carriers. Exemplary carriers for topical administration of compounds of this are mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

In certain embodiments, the invention provides a method for inhibitingcyclophilins in a positive manner in a patient or in a biological sample comprising the step of administering to said patient or contacting said biological sample with a compound according to the invention.

In certain embodiments, the invention is directed to the use of compounds of the invention and/or physiologically acceptable salts thereof, for inhibit cyclophilins. The compounds are characterized by such a high affinity to cyclophilins, which ensures a reliable binding and preferably inhibition of cyclophilins. In certain embodiments, the substances are mono-specific in order to guarantee an exclusive and directed recognition with the single cyclophilin target. In the context of the present invention, the term "recognition"—without being limited thereto—relates to any type of interaction between the specific compounds and the target, particularly covalent or non-covalent binding or association, such as a covalent bond, hydrophobic/hydrophilic interactions, van der Waals forces, ion pairs, hydrogen bonds, ligand-receptor interactions, and the like. Such association may also encompass the presence of other molecules such as peptides, proteins or nucleotide sequences. The present receptor/ligand-interaction is characterized by high affinity, high selectivity and minimal or even lacking cross-reactivity to other target molecules to exclude unhealthy and harmful impacts to the treated subject.

In certain embodiments, the present invention relates to a method for inhibiting cyclophilins with at least one compound of formula (I) according to the invention and/or physiologically acceptable salts thereof. In certain embodiments, the system is a cellular system. In other embodiments, the system is an in-vitro translation which is based on the protein synthesis without living cells. The cellular system is defined to be any subject provided that the subject comprises cells. Hence, the cellular system can be selected from the group of single cells, cell cultures, tissues, organs and animals. In certain embodiments, the method for inhibiting cyclophilins is performed in-vitro. The prior teaching of the present specification concerning the compounds of formula (I), including any embodiments thereof, is valid and applicable without restrictions to the compounds according to formula (I) and their salts when used in the method for inhibiting cyclophilins. The prior teaching of the present specification concerning the compounds of formula (I), including any embodiments thereof, is valid and applicable without restrictions to the compounds according to formula (I) and their salts when used in the method for inhibiting cyclophilins.

In certain embodiments, the invention provides a method for preventing, treating or ameliorating in a subject a disease, disorder, or condition that is causally related to the aberrant activity of cyclophilins, which comprises administering to the subject a therapeutically effective amount of a compound of any formulae herein, or a pharmaceutically acceptable salt thereof. In certain embodiments, the disease or disorder is a viral infections, inflammation, neurologic disorders, cardiac failure and cancer.

One aspect of this invention provides compounds or compositions that are inhibitors of cyclophilins, or pharmaceutically acceptable salts thereof, and thus are useful for treating or lessening the severity of a disease, condition, or disorder in a patient, wherein cyclophilins are implicated in the disease, condition, or disorder. The terms, "disease", "disorder", and "condition" may be used interchangeably here to refer to a cyclophilin mediated medical or pathological condition. The term "cyclophilin mediated condition", as used herein, means any disease state or other deleterious condition in which cyclophilins are known to play a role. The term "cyclophilin mediated condition" or "disease" also means those diseases or conditions that are alleviated by treatment with a cyclophilin inhibitor. As used herein, the terms "subject" and "patient" are used interchangeably. The terms "subject" and "patient" refer to an animal, and more specifically a human. In one embodiment, the subject is a non-human animal such as a rat or dog. In a preferred embodiment, the subject is a human.

In certain embodiments, the present invention provides a method for inhibiting cyclophilin activity in a patient comprising administering to the patient a compound or composition of the present invention. In another embodiment, the present invention provides a method for inhibiting cyclophilin activity in a biological sample comprising administering a compound or composition of the present invention.

In certain embodiments the invention provides a method of treating, preventing, or lessening the severity of a disease or condition of a patient selected from viral infections, inflammation, neurologic disorders, cardiac failure and cancer.

In certain embodiments, the invention provides compounds that are useful for the treatment of diseases, disorders, and conditions, e.g, viral disease, pneumonia, bacteremia, trauma, tuberculosis, parasitic disease, neuroinflammation, schizophrenia, depression, neurodegenerative disease, and pain.

In certain embodiments, the disease or disorder is Parkinson's disease, Alzheimer's disease, ALS, memory loss, hair loss, hearing loss, vision loss, stroke, peripheral neuropathy, diabetic neuropathy, mitochondrial disorder, viral infection, traumatic brain injury, or a spinal cord injury.

In certain embodiments, the neurodegenerative disease is selected from Alzheimer's disease, Parkinson's disease, Amyotrophic Lateral Sclerosis (ALS), Dementia, Multiple Sclerosis, and Huntington's disease.

In certain embodiments, the viral disease is selected from Human Immunodeficiency Virus (HIV), Hepatitis A-D, Human Papilloma Virus (HPV), and Herpes, including Herpes Simplex I and II, as well as the Epstein Barr Virus.

In certain embodiments, the invention provides for the treatment of diseases, disorders, and conditions characterized by excessive or abnormal cell proliferation. Such diseases include a proliferative or hyperproliferative disease. Examples of proliferative and hyperproliferative diseases include cancer and myeloproliferative disorders. In certain embodiments, the method is used to treat or prevent a condition selected from a proliferative or hyperproliferative disease, e.g., cancer.

In certain embodiments, the term "cancer" includes, but is not limited to the following cancers. Oral: head and neck, including buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: Non-small cell lung carcinoma including adenocarcinoma (acinar, bronchioloalveolar carcinoma [nonmucinous, mucinous, mixed], papillary, solid adenocarcionoma, clear cell, mucinous [colloid] adenocarcinoma, mucinous cystadenocarcinoma, signet ring, well-differentiated fetal), bronchioalveolar, squamous cell carcinoma (basaloid, clear cell, papillary, small cell), large cell (undifferentiated) carcinoma (giant cell, basaloid, clear cell, large cell [with rhabdoid phenotype], large cell neuroendocrine carcinoma [LCNEC], combined LCNEC); small cell lung cancer including small cell (oat cell) carcinoma, combined small cell; adenoid cystic carcinoma; hamartoma; lymphoma; neuroendocrine/carcinoid; sarcoma. Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Female/Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma, undifferentiated thyroid cancer, medullary thyroid carcinoma, multiple endocrine neoplasia type 2A, multiple endocrine neoplasia type 2B, familial medullary thyroid cancer, pheochromocytoma, paraganglioma; and Adrenal glands: neuroblastoma.

In certain embodiments, the invention provides compounds that are useful for the treatment of diabetes or protozoan parasites (e.g., *Leishmania* or *Plasmodium falciparum*).

The invention furthermore relates to a medicament comprising at least one compound according to the invention and/or pharmaceutically usable derivatives, salts, solvates and stereoisomers thereof, including mixtures thereof in all ratios. In certain embodiments, the invention relates to a medicament comprising at least one compound according to the invention and/or physiologically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with cyclophilin activity, in such a way that a pathogenic modification of their overall condition or of the condition of particular regions of the organism could establish at least temporarily.

In another aspect, the invention provides for a kit consisting of separate packs of an effective amount of a compound according to the invention and/or pharmaceutically acceptable salts, derivatives, solvates and stereoisomers thereof, including mixtures thereof in all ratios, and optionally, an effective amount of a further active ingredient. The kit comprises suitable containers, such as boxes, individual bottles, bags or ampoules. The kit may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further active ingredient in dissolved or lyophilized form.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent or delay their recurrence.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 100 mg/kg and preferably from about 1 mg/kg to about 50 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are formulated according to the known art using suitable dispersing or wetting agents and suspending agents. The sterile injectable preparation are also a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This is accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also optionally comprises buffering agents.

Solid compositions of a similar type are also employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type are also employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also comprise, as is normal practice, additional substances other than inert diluents, e.g., tableting lubricants and other tableting aids such a magnesium stearate and microcrystalline cellulose. In the case of capsules, tablets and pills, the dosage forms optionally also comprise buffering agents. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein. Compound numbers utilized in the Examples below correspond to compound numbers set forth supra.

General Conditions and Analytical Methods

All solvents used were commercially available and were used without further purification. Reactions were typically run using anhydrous solvents under an inert atmosphere of nitrogen.

All NMR experiments were recorded on a Bruker AVANCE 500 NMR Spectrometer equipped with a Bruker 5 mm PABBO BB-1H/D Z-GRD at 500 MHz for proton NMR or a Bruker Avance III 400. LC-MS analyses were performed on a WATERS Alliance LC-MS machine consisting of an HPLC Alliance 2690 system, a Photodiode Array Detector Waters 2996, an Evaporative Light Scattering Detector (ELSD) Sedex 75 and a Mass spectrometer micromass ZQ Waters. The column used was a Sunfire C18, 3.5 µm, 2.1×50 mm. A linear gradient was applied, starting at 100% A (A: water+0.04% HCOO⁻, $NH_4^+$ (10 mM)) and ending at 100% B (B: acetonitrile+HCOO⁻, $NH_4^+$ (10 mM)) over 3.1 min with a total run time of 6 min. The column temperature was at 25° C. with the flow rate at 0.7 mL/min. The Diode Array Detector was scanned from 200-400 nm. The mass spectrometer was equipped with an electro spray ion source (ES) operated in a positive or negative mode. The mass spectrometer was scanned between m/z 50-1000 with a scan time of 0.5 s. In some examples, LC-MS analyses were performed on Agilent 1200 Series mass spectrometers from Agilent Technologies, using either Atmospheric Chemical Ionization (APCI) or Electrospray Ionization (ESI). Column: XBridge C8, 3.5 µm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B or a LC/MS Waters ZMD (ESI).

The following abbreviations refer to the abbreviations used below: DCM (dichloromethane), DIPEA (diisopropylamine), DMF (dimethylformamide), EDCI (1-Ethyl[3-(dimethylamino)propyl]carbodiimide), EtOAc (Ethyl acetate), HOPO (2-pyridinol-oxide), 0/N (overnight), HPLC (High Pressure Liquid Chromatography), RT (room Temperature), TBAB (tetrabutylammonium bromide), TBAF (tetrabutylammonium fluoride), TBDMS (tert-butyldimethylsilyl), TBTU (2-(1H-Benzotriazole-1-yl)-1,1,3,3-tetramethyluronium tetrafluoroborate), TEA (trimethylamine), THF (tetrahydrofurane), TFA (trifluoro acetic acid).

Intermediate 1 and 2: tert-butyl (((2S,3S,6S)-3-hydroxy-2,3,4,6-tetrahydro-1H-2,6-methanobenzo[c][1,5]oxazocin-8-yl)methyl)carbamate and tert-butyl (((2R,3S,6R)-3-hydroxy-2,3,4,6-tetrahydro-1H-2,6-methanobenzo[c][1,5]oxazocin-8-yl)methyl)carbamate

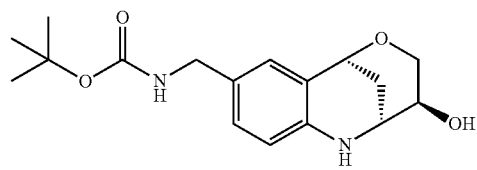

Chiral

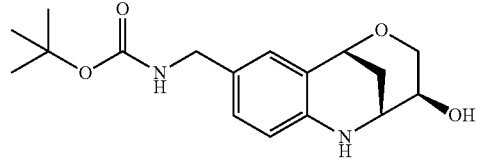

Chiral

A mixture of 2-Deoxy-D-ribose (Apollo, 6 g, 44.3 mmol), (4-Amino-benzyl)-carbamic acid tert-butyl ester (Acros, 1.52 g, 66 mmol) and montmorillonite (45 g) was stirred at RT in MeCN for five days. The reaction mixture was then filtered through a celite pad which was subsequently washed with EtOAc. The filtrate was concentrated under reduced pressure. Purification of this crude (16 g) by flash chromatography on silica (Cyclohexane: EtOAc, gradient from 7:3 to 3:7) afforded the title compounds:

First eluting fraction: tert-butyl (((2S,3S,6S)-3-hydroxy-2,3,4,6-tetrahydro-1H-2,6-methanobenzo[c][1,5]oxazocin-8-yl)methyl)carbamate (5.24 g, 36.5%), beige solid, Rf=0.35 (Cyclohexane:EtOAc, 2:8), 1H NMR (CDCl$_3$): 7.09 (dd, 1H, J=8.0 Hz, J=2.0 Hz), 7.04 (d, 1H, J=2.0 Hz), 6.62 (d, 1H, J=8.0 Hz), 4.73 (brs, 1H), 4.67 (brs, 1H), 4.26-4.09 (m, 2H), 3.81-3.75 (m, 1H), 3.75-3.68 (m, 1H), 3.67-3.63 (m, 1H), 2.90 (t, 1H, J=11.0 Hz), 2.13 (ddd, 1H, J=13.2 Hz, J=3.5 Hz, J=2.3 Hz), 1.88 (ddd, 1H, J=13.2 Hz, J=4.6 Hz, J=1.8 Hz), 1.46 (s, 9H).

Second eluting fraction: tert-butyl (((2R,3S,6R)-3-hydroxy-2,3,4,6-tetrahydro-1H-2,6-methanobenzo[c][1,5]oxazocin-8-yl)methyl)carbamate (5.6 g, 39%), white solid, Rf=0.25 (Cyclohexane:EtOAc, 2:8), 1H NMR (CDCl$_3$): 7.09 (dd, 1H, J=8.0 Hz, J=2.0 Hz), 7.06 (d, 1H, J=2.0 Hz), 6.53 (d, 1H, J=8.0 Hz), 4.74 (brs, 1H), 4.67 (brs, 1H), 4.25-4.14 (m, 2H), 3.68-3.64 (m, 1H), 3.59-3.47 (m, 3H), 2.60-2.53 (m, 1H), 1.59-1.52 (m, 1H), 1.45 (s, 9H).

Intermediate 3: ((2S,3S,6S)-3-((tert-butyldimethylsilyl)oxy)-2,3,4,6-tetrahydro-1H-2,6-methanobenzo[c][1,5]oxazocin-8-yl)methanamine Step 1: Formation of tert-butyl (((2S,3S,6S)-3-((tert-butyldimethylsilyl)oxy)-2,3,4,6-tetrahydro-1H-2,6-methanobenzo[c][1,5]oxazocin-8-yl)methyl)carbamate

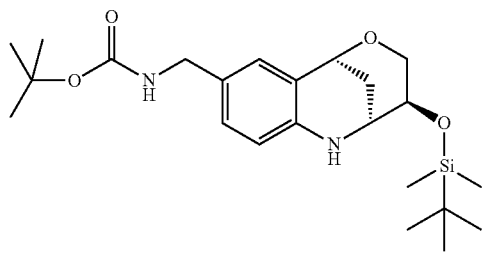

Chiral

A solution of tert-butyl (((2S,3S,6S)-3-hydroxy-2,3,4,6-tetrahydro-1H-2,6-methanobenzo[c][1,5]oxazocin-8-yl)methyl)carbamate (intermediate 1, 5.2 g, 16.2 mmol) and lutidine (5.8 mL, 49 mmol) in DCM (150 mL) was stirred at 0° C. before the addition of TBDMSOTf (6.2 g, 24.3 mmol). The reaction mixture was allowed to reach RT and was stirred for 4 days. The reaction mixture was then diluted with DCM (50 mL) and washed with aqueous solution of HCl 1M (50 mL). The aqueous phase was extracted with DCM (3×50 mL) and combined organic phases were washed with brine (2×50 mL), dried over Na$_2$SO$_4$, filtered, and concentrated. Purification by flash chromatography on silica (cyclohexane: EtOAc, gradient from 10:0 to 8:3) afforded the title compound as a white amorphous solid (4.2 g, 59%). 1H NMR (CDCl$_3$): 7.08 (dd, 1H, J=8.0 Hz, J=2.0 Hz), 7.00 (d, 1H, J=2.0 Hz), 6.63 (d, 1H, J=8.0 Hz), 4.70 (brs, 1H), 4.64-4.61 (m, 1H), 4.26-4.09 (m, 2H), 3.84 (ddd, 1H, J=10.5 Hz, J=6.0 Hz, J=3.3 Hz), 3.55 (dd, 1H, J=11.5 Hz, J=6.0 Hz), 3.50-3.45 (m, 1H), 3.00 (t, 1H, J=11.0 Hz), 2.15 (ddd, 1H, J=13.3 Hz, J=3.6 Hz, J=2.4 Hz), 1.98 (ddd, 1H, J=13.3 Hz, J=8.8 Hz, J=1.8 Hz), 1.45 (s, 9H), 0.89 (s, 9H), 0.09 (s, 3H), 0.04 (s, 3H).

Step 2: formation of ((2S,3S,6S)-3-((tert-butyldimethylsilyl)oxy)-2,3,4,6-tetrahydro-1H-2,6-methanobenzo[c][1,5]oxazocin-8-yl)methanamine

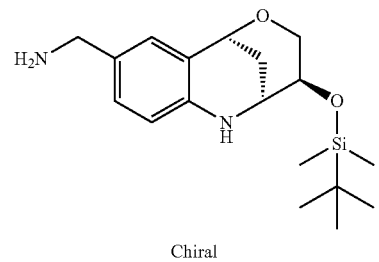 [SMILES: CC(C)(C)[Si](C)(C)O[C@@H]1CO[C@H]2C[C@@H]1Nc1ccc(CN)cc12]

Chiral

TFA (14.8 mL) was added slowly to a solution of tert-butyl (((2S,3S,6S)-3-((tert-butyldimethylsilyl)oxy)-2,3,4,6-tetrahydro-1H-2,6-methanobenzo[c][1,5]oxazocin-8-yl)methyl)carbamate (4.2 g, 9.66 mmol) in DCM (200 mL) maintained at 0° C. The mixture was then allowed to warm at RT and stirred for 1 h. It was then cooled down again at 0° C. and slowly quenched with an aqueous solution of NaOH 10% (100 mL). The aqueous phase was extracted with DCM (2×50 mL) and the combined organic phases were washed with water (2×50 mL), Brine (2×50 mL), dried over Na$_2$SO$_4$, filtered and concentrated to give the title compound as a beige solid (2.99 g, 100%). 1H NMR (CDCl$_3$): 7.09 (dd, 1H, J=8.2 Hz, J=2.1 Hz), 7.03 (d, 1H, J=2.1 Hz), 6.62 (d, 1H, J=8.2 Hz), 4.65-4.62 (m, 1H), 4.58 (brs, 1H), 3.84 (ddd, 1H, J=10.4 Hz, J=6.0 Hz, J=3.3 Hz), 3.74 (s, 2H), 3.55 (dd, 1H, J=11.6 Hz, J=6.0 Hz), 3.50-3.45 (m, 1H), 3.02 (t, 1H, J=11.0 Hz), 2.18-2.11 (m, 1H), 1.98 (ddd, 1H, J=13.2 Hz, J=4.4 Hz, J=1.6 Hz), 1.79 (s, 2H), 0.89 (s, 9H), 0.09 (s, 3H), 0.04 (s, 3H).

Intermediate 4: ((2R,3S,6R)-3-((tert-butyldimethylsilyl)oxy)-2,3,4,6-tetrahydro-1H-2,6-methanobenzo[c][1,5]oxazocin-8-yl)methanamine

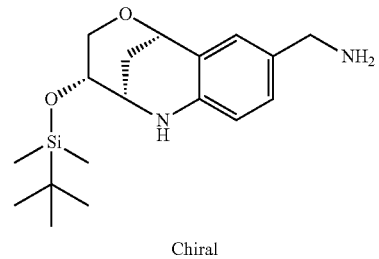 [SMILES: CC(C)(C)[Si](C)(C)O[C@@H]1CO[C@@H]2C[C@H]1Nc1ccc(CN)cc12]

Chiral

The title compound was prepared following a similar procedure as described for intermediate 3 from tert-butyl (((2R,3S,6R)-3-hydroxy-2,3,4,6-tetrahydro-1H-2,6-methanobenzo[c][1,5]oxazocin-8-yl)methyl)carbamate (Intermediate 2). 1H NMR (CDCl$_3$): 7.12-7.08 (m, 2H), 6.51 (d, 1H, J=7.5 Hz), 4.71-4.68 (m, 1H), 4.32 (d, 1H, J=3.8 Hz), 3.76 (s, 2H), 3.51-3.44 (m, 3H), 3.38 (dd, 1H, J=12.7 Hz, J=1.8 Hz), 3.70-3.60 (m, 1H), 2.06 (bs, 3H), 1.50-1.44 (m, 1H), 0.93 (s, 9H), 0.09 (s, 3H), 0.08 (s, 3H).

Intermediate 5: (exo)-3,5-Dioxo-4-aza-tricyclo [5.2.1.0²,⁶]dec-4-yl)-acetic acid Step 1: Ethyl-(exo)-3,5-Dioxo-4-aza-tricyclo [5.2.1.0²,⁶]dec-4-yl)-acetic acetate

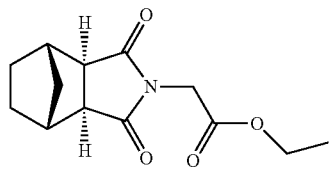 [SMILES: CCOC(=O)CN1C(=O)[C@@H]2[C@H]3CC[C@H](C3)[C@@H]2C1=O]

A mixture of bicyclo[2.2.1]heptane-2,3-di-exo-carboximide (prepared as described in Chem. Pharm. Bull., 1991 p 2288; 1.0 g, 6.05 mmol), ethyl chloroacetate (1.3 mL, 12.1 mmol), TBAB (39 mg, 0.12 mmol) and potassium carbonate (1.17 g, 8.48 mmol) were irradiated in microwawe for 10 min at 150° C. (150 W). The mixture was then diluted with water and EtOAc. Organic phase was separated, and aqueous phase was extracted with EtOAc (3×15 mL). Combined organic phases were washed with brine (1×15 mL), dried over Na₂SO₄, filtered and concentrated to afford the title compound as a brown oil (1.74 g, 114%).

Step 2: Formation of (exo)-3,5-Dioxo-4-aza-tricyclo [5.2.1.0²,⁶]dec-4-yl)-acetic acid

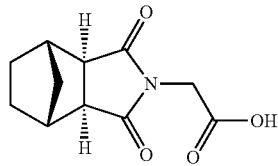 [SMILES: O=C(O)CN1C(=O)[C@@H]2[C@H]3CC[C@H](C3)[C@@H]2C1=O]

A mixture of Ethyl-(exo)-3,5-Dioxo-4-aza-tricyclo [5.2.1.0²,⁶]dec-4-yl)-acetic acetate (1.52 g, 6.05 mmol) and LiOH.H₂O (1.02 g, 24.2 mmol) in THF (20 mL), MeOH (4 mL) and water (2 mL) was stirred at RT for 18 h. The mixture was then diluted with aq. sat. NH₄Cl, acidified with HCl (1M aq. Solution) and extracted with EtOAc (3×). The combined organic phases were washed with brine, dried over Na₂SO₄, filtered and concentrated. The crude was triturated in DCM, filtered and dried to give the title compound as a beige solid (610 mg, 45%). 1H NMR (CD₃OD): 3.97 (d, 1H, J=17.8 Hz), 3.71 (d, 1H, J=17.8 Hz), 2.74 (brd, 1H, J=9.8 Hz), 2.62 (dd, 1H, J=9.8 Hz, J=1.5 Hz), 2.55-2.49 (m, 1H), 2.44-2.98 (m, 1H), 2.21-2.15 (m, 1H), 1.65-1.53 (m, 2H), 1.32-1.18 (m, 3H).

Intermediate 6: 8-Aminomethyl-5-ethyl-2,3,5,6-tetrahydro-1H-benzo[b][1,5]diazocin-4-one Step 1: Formation of 4-Bromo-3-ethylaminomethyl-benzonitrile

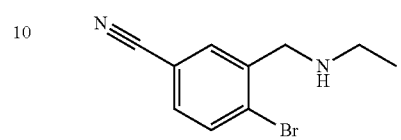

A mixture of 5-cyano-2-bromobenzaldehyde (Accela, 5.0 g, 24 mmol) and ethylamine (3.6 mL, 48 mmol) in toluene (380 mL) was stirred at RT for 1 h. The mixture was then heated to 130° C. with a Dean-Stark for 3 h. After cooling to RT, the solvent was removed under reduced pressure and the residue was dissolved in MeOH (54 mL). NaBH₄ (1.81 g, 48 mmol) was added portion-wise at 0° C. and the resulting mixture was stirred at RT for 18 h. After cooling to 0° C., sat. aq. NaHCO₃ (50 mL) was added slowly and the mixture was extracted with DCM (3×). The combined organic phases were dried over Na₂SO₄, filtered and concentrated to give the title compound (5.68 g, 99%) which was used directly in the next step.

¹H NMR (CDCl₃): 7.76 (d, 1, J=2.0 Hz), 7.64 (d, 1, J=8.2 Hz), 7.38 (dd, 1, J=8.2 Hz, J=2.0 Hz), 3.88 (s, 2), 2.69 (q, 2, J=7.1 Hz), 1.16 (t, 3, J=7.1 Hz).

Step 2: Formation of 5-Ethyl-4-oxo-1,2,3,4,5,6-hexahydro-benzo[b][1,5]diazocine-8-carbonitrile

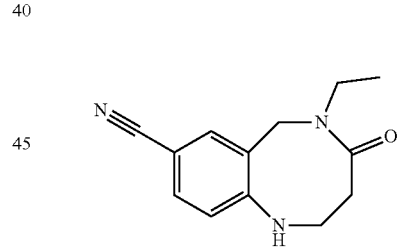

To a stirred solution of 4-Bromo-3-ethylaminomethyl-benzonitrile (4.68 g, 19.6 mmol) in toluene (50 mL) were added successively azetidin-2-one (1.67 g, 23.5 mmol), N,N'-dimethylethylendiamine (72 mg, 1.96 mmol), CuI (186 mg, 0.98 mmol) and K₂CO₃ (5.4 g, 39 mmol) at RT and the resulting mixture was heated to 110° C. for 6 h and 90° C. for 16 h. After cooling to RT, the mixture was filtered through Celite®, the cake was washed thoroughly with DCM and the solvent was removed under reduced pressure. Purification by flash column chromatography on silica (EtOAc followed by 3% MeOH in DCM) afforded the title compound as a yellow solid (1.4 g, 31%). ¹H NMR (CDCl₃): 7.36 (m, 2), 6.66 (d, 1, J=8.8 Hz), 4.62 (bs, 1), 4.55 (s, 2), 3.61 (m, 2), 3.23 (q, 2, J=7.1 Hz), 3.01 (t, 2, J=6.5 Hz), 1.16 (t, 3, J=7.1 Hz).

Step 3: Formation of 8-Aminomethyl-5-ethyl-2,3,5,6-tetrahydro-1H-benzo[b][1,5]diazocin-4-one

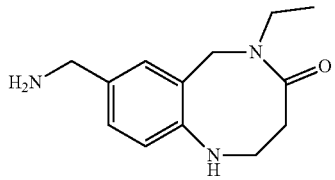 [SMILES: CCN1Cc2cc(CN)ccc2NCCC1=O]

A solution of 5-Ethyl-4-oxo-1,2,3,4,5,6-hexahydro-benzo[b][1,5]diazocine-8-carbonitrile (550 mg, 2.4 mmol) in MeOH (36 mL) and NH$_3$ (14 mL of a 7 M solution in MeOH) was hydrogenated using Raney Nickel as catalyst in a ThalesNano, H-Cube® system (50 bars H$_2$, flow rate of 1 mL/min). Concentration of the resulting solution afforded the title compound as a yellow solid (550 mg, 98%). 1H NMR (CDCl$_3$): 7.08 (m, 2), 6.71 (d, 1, J=7.9 Hz), 4.45 (s, 2), 3.80 (s, 2), 3.69 (m, 4), 2.93 (t, 2, J=6.0 Hz), 1.10 (t, 3, J=7.1 Hz).

Example 1: 2-exo-(3,5-Dioxo-4-aza-tricyclo[5.2.1.02,6]dec-4-yl)-N-((1R,9R,10S)-10-hydroxy-12-oxa-8-aza-tricyclo[7.3.1.02,7]trideca-2(7),3,5-trien-4-ylmethyl)-acetamide Step 1: Formation of N-{[(1R,9R,10S)-10-{[dimethyl(propan-2-yl)silyl]oxy}-12-oxa-8-azatricyclo[7.3.1.0$^{2,7}$]trideca-2(7),3,5-trien-4-yl]methyl}-2-[(exo)-3,5 dioxo-4-azatricyclo[5.2.1.0$^{2,6}$]decan-4-yl]acetamide

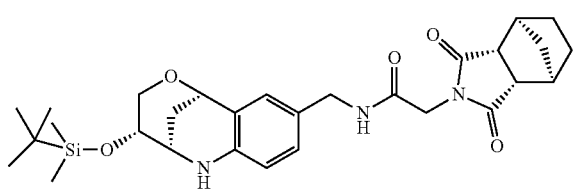 [SMILES: CC(C)(C)[Si](C)(C)O[C@@H]1CO[C@@H]2C[C@H]1Nc1ccc(CNC(=O)CN3C(=O)[C@@H]4[C@H]5CC[C@H](C5)[C@@H]4C3=O)cc12]

A solution of exo-3,5-Dioxo-4-aza-tricyclo[5.2.1.02,6]dec-4-yl)-acetic acid (intermediate 5, 183 mg, 0.82 mmol), EDCI (161 mg, 0.82 mmol), HOPO (93 mg, 0.82 mmol) and DIPEA (146 mg, 1.12 mmol) in DMF (6 mL) was stirred at RT for 10 min before the addition of ((2R,3S,6R)-3-((tert-butyldimethylsilyl)oxy)-2,3,4,6-tetrahydro-1H-2,6-methanobenzo[c][1,5]oxazocin-8-yl)methanamine (intermediate 4, 250 mg, 0.75 mmol). The reaction mixture was then stirred at 50° C. for 24 h. It was diluted with EtOAc (20 mL), washed with sat. NH$_4$Cl (1×10 mL), water (1×10 mL) and brine (2×10 mL). Organic phase was dried over Na$_2$SO$_4$, filtrated and concentrated. Purification by flash chromatography on silica (Cyclohexanee:EtOAc, Gradient 10:0 to 0:10) afforded the title compound as a yellow oil (88 mg, 22%). $^1$H NMR (CDCl$_3$): 7.08-7.02 (m, 2H), 6.50 (d, 1H, J=7.9 Hz), 5.74-5.65 (m, 1H), 4.70-4.66 (m, 1H), 4.40-4.34 (m, 1H), 4.32 (t, 1H, 5.1 Hz), 4.11 (d, 1H, J=2.1 Hz), 3.52-3.45 (m, 3H), 3.37 (dd, 1H, J=13.2 Hz, J=1.5 Hz), 2.70-2.64 (m, 5H), 1.71-1.39 (m, 5H), 1.38-1.31 (m, 2H), 1.28-1.21 (m, 2H), 0.94 (s, 9H), 0.10 (s, 3H), 0.09 (s, 3H).

Step 2: Formation of 2-(exo-3,5-Dioxo-4-aza-tricyclo[5.2.1.02,6]dec-4-yl)-N-((1R,9R,10S)-10-hydroxy-12-oxa-8-aza-tricyclo[7.3.1.02,7]trideca-2(7),3,5-trien-4-ylmethyl)-acetamide

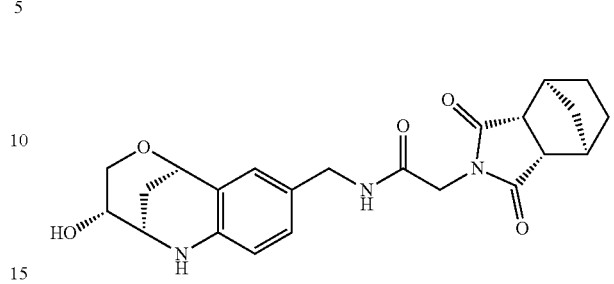

A mixture of N-{[(1R,9R,10S)-10-{[dimethyl(propan-2-yl)silyl]oxy}-12-oxa-8 azatricyclo[7.3.1.0$^{2,7}$]trideca-2(7),3,5-trien-4-yl]methyl}-2-[(exo)-3,5 dioxo-4-azatricyclo[5.2.1.0$^{2,6}$]decan-4-yl]acetamide (118 mg, 0.22 mmol) and TBAF (114 mg, 0.44 mmol) in THF (95 mL) was stirred at RT for 20 h. THF was removed under reduced pressure and the crude was dissolved in DCM, washed with sat. NaHCO$_3$, water and brine. Organic phase was dried over Na$_2$SO$_4$, filtered and concentrated. Purification by flash chromatography on silica (DCM:MeOH:NH$_4$OH, 90:10:1) afforded the title compound as a white solid (17 mg, 18%). $^1$H NMR (CDCl$_3$, 500 MHz): 7.03 (dd, 1H, J=8.2 Hz, J=2.2 Hz), 6.98 (d, 1H, J=2.2 Hz), 6.55 (d, 1H, J=8.2 Hz), 4.64 (s, 1H), 4.22 (dd, 2H, J=20 Hz, J=14.5 Hz), 4.11 (s, 2H), 3.54-3.51 (m, 1H), 3.49 (dd, 1H, J=12.5 Hz, J=1.0 Hz), 3.45-3.41 (m, 1H), 3.37 (dd, 1H, J=12.5 Hz, J=2 Hz), 2.71 (d, 2H, J=1.0 Hz), 2.61 (d, 2H, J=2.0 Hz), 2.59 (dt, 1H, J=13.0 Hz, J=3.0 Hz, J=3.0 Hz), 1.73-1.62 (m, 2H), 1.58-1.54 (m, 1H), 1.45-1.35 (m, 3), 1.21 (dt, 1H, J=11.0 Hz, J=1.3 Hz, J=1.3 Hz). LC/MS: 428.1 (M+1), 98.7% purity (Sunfire, 254 nm).

Example 2: 2-endo-(3,5-Dioxo-4-aza-tricyclo[5.2.1.02,6]dec-4-yl)-N-(1,2,3,4-tetrahydro-quinolin-6-ylmethyl)-acetamide

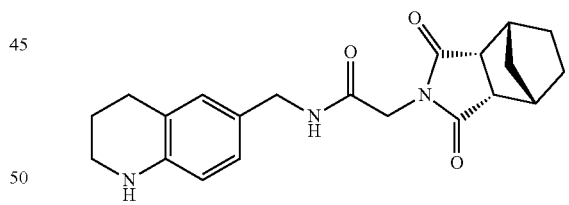

2,4,6-Tripropyl-[1,3,5,2,4,6]trioxatriphosphinane 2,4,6-trioxide (T$_3$P=50 wt. % in EtOAc, 0.80 mL; 1.34 mmol) was added to a solution of endo-(3,5-Dioxo-4-aza-tricyclo[5.2.1.02,6]dec-4-yl)-acetic acid (Matrix scientific, 150 mg; 0.67 mmol), C-(1,2,3,4-Tetrahydro-quinolin-6-yl)-methylamine (Enamine, 127 mg; 0.73 mmol) and TEA (280 μl; 2.00 mmol) in DCM (5.0 mL) maintained at 0° C. The reaction mixture was then stirred at RT for 12 h. It was diluted with dichloromethane (1×20 mL), washed with water (1×20 mL), and brine (1×20 mL), dried over Na$_2$SO$_4$, filtered and concentrated. Purification by flash chromatography on silica (Pet.Ether:EtOAc, 40:50) afforded the title compound as an off-white solid (105 mg, 42%).

$^1$H NMR (400 MHz, DMSO-d6): 8.35 (t, J=5.60 Hz, 1H), 6.72 (d, J=6.52 Hz, 2H), 6.35 (t, J=2.36 Hz, 1H), 5.56 (s,

1H), 4.04 (d, J=5.56 Hz, 2H), 3.94 (s, 2H), 3.13 (t, J=5.60 Hz, 4H), 2.61 (t, J=6.40 Hz, 2H), 2.56 (s, 2H), 1.79-1.73 (m, 2H), 1.60 (d, J=9.68 Hz, 1H), 1.50 (d, J=9.60 Hz, 1H), 1.43-1.35 (m, 4H). LC/MS: 368.0 (M+1), 97.6% purity (X-Terra, 254 nm).

Example 3: 2-endo-1,3-dioxohexahydro-1H-4,7-methanoisoindol-2(3H)-yl)-N-(((2R,3S,6R)-3-hydroxy-2,3,4,6-tetrahydro-1H-2,6-methanobenzo[c][1,5]oxazocin-8-yl)methyl)acetamide

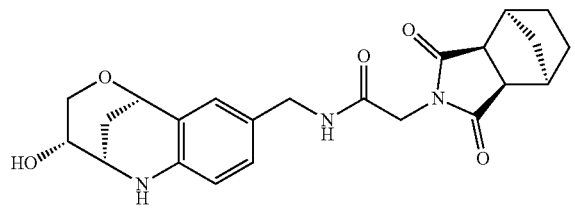 [SMILES: O=C(CN1C(=O)[C@@H]2[C@@H]3CC[C@@H](C3)[C@@H]2C1=O)NCc1ccc2c(c1)[C@H]1C[C@@H](N2)[C@H](O)CO1]

The title compound was prepared following a similar procedure as described for example 1 from ((2R,3S,6R)-3-((tert-butyldimethylsilyl)oxy)-2,3,4,6-tetrahydro-1H-2,6-methanobenzo[c][1,5]oxazocin-8-yl)methanamine (Intermediate 4, 139 mg, 0.42 mmol) and (endo)-3,5-Dioxo-4-aza-tricyclo[5.2.1.02,6]dec-4-yl)-acetic acid (Matrix scientific, 93 mg, 0.42 mmol) as an orange solid (27 mg, 15%, 2 steps). $^1$H NMR (500 MHz, CD$_3$OD): 7.04 (dd, 1H, J=8.5 Hz, J=2.0 Hz), 7.00 (d, 1H, J=2.0 Hz), 6.56 (d, 1H, J=8.5 Hz), 4.65 (bs, 1H), 4.26 (d, 1H, J=14.5 Hz), 4.22 (d, 1H, J=14.5 Hz), 4.11 (s, 2H), 3.55-3.47 (m, 2H), 3.45-3.42 (m, 1H), 3.39 (dd, 1H, J=12.5 Hz, J=2.0 Hz), 3.20-3.18 (m, 2H), 2.72-2.66 (m, 2H), 2.61 (ddd, 1H, J=13.0 Hz, J=3.4 Hz, J=2.8 Hz), 1.74-1.69 (m, 1H), 1.64 (dt, 1H, J=10.0 Hz, J=1.5 Hz, J=1.5 Hz), 1.58-1.51 (m, 2H), 1.47-1.41 (m, 3H). LC/MS: 426.0 (M+1), 96.9% purity (Sunfire, 254 nm).

Example 4: N-endo-(4-Amino-benzyl)-2-(3,5-dioxo-4-aza-tricyclo[5.2.1.02,6]dec-4-yl)-acetamide Step 1: 2-endo-(3,5-Dioxo-4-aza-tricyclo[5.2.1.02,6]dec-4-yl)-N-(4-nitro-benzyl)-acetamide

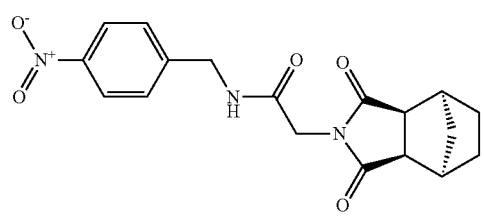 [SMILES: O=C(CN1C(=O)[C@@H]2[C@@H]3CC[C@@H](C3)[C@@H]2C1=O)NCc1ccc([N+](=O)[O-])cc1]

The title compound was prepared following a similar procedure as described for example 2 from endo-(3,5-Dioxo-4-aza-tricyclo[5.2.1.02,6]dec-4-yl)-acetic acid (Matrix scientific, 200 mg; 0.90 mmol) and 4-Nitro-benzylamine hydrochloride (192 mg; 0.99 mmol) as a yellow solid (170 mg; 0.47 mmol; 52.8%). 1H NMR (400 MHz, DMSO-d6): 8.82 (t, J=5.92 Hz, 1H), 8.21-8.17 (m, 2H), 7.51 (d, J=8.80 Hz, 2H), 4.42 (d, J=5.96 Hz, 2H), 4.05 (s, 2H), 3.13 (s, 2H), 2.57 (s, 2H), 1.60 (d, J=9.60 Hz, 1H), 1.50 (d, J=9.64 Hz, 1H), 1.40 (t, J=6.12 Hz, 2H), 1.33 (d, J=8.44 Hz, 2H). LC/MS: 358 (M+1), 99% purity (X-Bridge-254 nm).

Step 2: Formation of N-endo-(4-Amino-benzyl)-2-(3,5-dioxo-4-aza-tricyclo[5.2.1.02,6]dec-4-yl)-acetamide

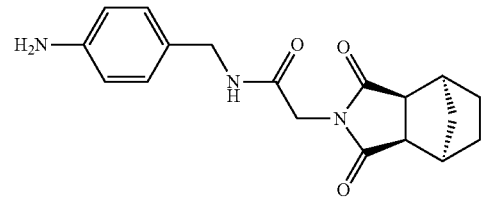 [SMILES: Nc1ccc(CNC(=O)CN2C(=O)[C@@H]3[C@@H]4CC[C@@H](C4)[C@@H]3C2=O)cc1]

Iron powder (75 mg; 1.34 mmol) was added to a solution of 2-endo-(3,5-Dioxo-4-aza-tricyclo[5.2.1.02,6]dec-4-yl)-N-(4-nitro-benzyl)-acetamide (160 mg; 0.45 mmol) and Ammonium Chloride (243 mg; 4.45 mmol) in Ethanol (9 mL) and water (1 mL) maintained at 85° C. the reaction mixture was then stirred at the same temperature for 30 min. It was allowed to cool to RT and diluted with DCM. Organic phase was washed with water (1×20 mL), brine (1×20 mL), dried over anhydrous sodium sulfate, filtered and concentrated. The solid obtained was washed with Hexane and dried under vacuum to afford the title compound as an off-white solid (120 mg, 81%). 1H NMR (400 MHz, DMSO-d6): 8.38 (t, J=5.64 Hz, 1H), 6.89 (d, J=8.36 Hz, 2H), 6.51-6.48 (m, 2H), 4.98 (s, 2H), 4.08 (d, J=5.60 Hz, 2H), 3.95 (s, 2H), 3.12 (s, 2H), 2.56 (s, 2H), 1.60 (d, J=9.64 Hz, 1H), 1.50 (d, J=9.64 Hz, 1H), 1.43-1.35 (m, 4H). LC/MS: 328 (M+1), 96% purity (X-Bridge-Maxplot).

Example 5: 2-endo-(3,5-Dioxo-4-aza-tricyclo[5.2.1.02,6]dec-4-yl)-N-[1-(4-amino-phenyl)-cyclopropyl]-acetamide

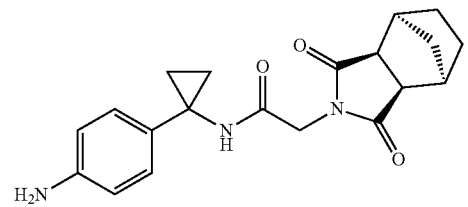 [SMILES: Nc1ccc(C2(NC(=O)CN3C(=O)[C@@H]4[C@@H]5CC[C@@H](C5)[C@@H]4C3=O)CC2)cc1]

The title compound was prepared following a similar procedure as described for example 4 from endo-(3,5-Dioxo-4-aza-tricyclo[5.2.1.02,6]dec-4-yl)-acetic acid (Matrix Scientific, 200 mg; 0.9 mmol) and 1-(4-Nitro-phenyl)-cyclopropylamine (170 mg; 9 mmol) as a white solid (45 mg, 15%—two steps). $^1$H NMR (DMSO-d6, 400 MHz) 8.70 (s, 1H), 6.82-6.80 (t, J=2.0 Hz, 2H), 6.44-6.42 (t, J=8.8 Hz, 2H), 4.85 (s, 2H), 3.94 (s, 2H), 3.10 (s, 2H), 2.55-2.49 (m, 2H), 1.60-1.57 (m, 1H), 1.50-1.47 (m, 1H), 1.40-1.30 (m, 4H), 0.96 (s, 4H). LC/MS: 354.2 (M+1), 97.3% purity (X-Bridge-Maxplot).

Example 6: 2-exo-3,5-Dioxo-4-aza-tricyclo[5.2.1.02,6]dec-4-yl)-N-(5-ethyl-4-oxo-1,2,3,4,5,6-hexahydro-benzo[b][1,5]diazocin-8-ylmethyl)-acetamide

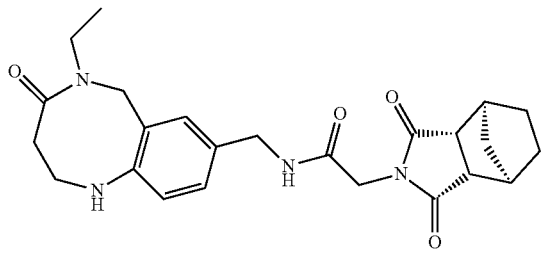

A mixture of (exo)-3,5-Dioxo-4-aza-tricyclo[5.2.1.02,6]dec-4-yl)-acetic acid (intermediate 5, 47 mg, 0.24 mmol), TEA (60 µl, 0.42 mmol) and TBTU (101 mg, 0.32 mmol) in DMF (1 mL) was stirred at RT for 10 min before the addition of 8-Aminomethyl-5-ethyl-2,3,5,6-tetrahydro-1H-benzo[b][1,5]diazocin-4-one (intermediate 6, 49 mg, 0.21 mmol). The resulting mixture was further stirred at RT for 12 h and 1 h at 50° C. The solvent was removed under reduced pressure and the residue was dissolved in EtOAc (10 mL). Organic phase was washed successively with aq. sat. NaHCO$_3$ (2×3 mL), aq. sat. NH$_4$Cl (2×3 mL), brine, dried over Na$_2$SO$_4$, filtered and concentrated. Purification by preparative TLC (EtOAc:MeOH, 92:9) afforded the title compound as a white solid (20 mg, 23%). $^1$H NMR (CDCl$_3$, 500 MHz): 7.02-6.99 (m, 2), 6.65 (d, 1, J=7.9 Hz), 6.41 (brs, 1), 4.41 (s, 2), 4.34 (d, 2, J=5.6 Hz), 4.12 (s, 2), 4.05 (brs, 1), 3.34 (t, 2, J=6.3 Hz), 3.25 (q, 2, J=7.1 Hz), 2.88 (t, 2, J=6.3 Hz), 2.72 (s, 2), 2.65 (s, 2), 1.67 (mm, 2), 1.59 (mm, 1), 1.34 (m, 2), 1.22 (m, 1), 1.05 (t, 3, J=7.1 Hz). LC/MS: 439.2 (M+1), 100% purity (Sunfire, 254 nm).

Example 7: N-[2-(4-Amino-phenyl)-ethyl]-2-(1,3-dioxo-octahydro-isoindol-2-yl)-acetamide

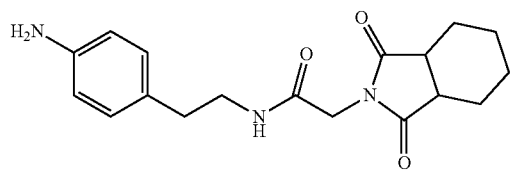 [SMILES: Nc1ccc(CCNC(=O)CN2C(=O)C3CCCCC3C2=O)cc1]

The title compound was prepared following a similar procedure as described for example 4 from (1,3-Dioxo-octahydro-isoindol-2-yl)-acetic acid (Enamine, 200 mg; 0.87 mmol) and 2-(4-Nitro-phenyl)-ethylamine hydrochloride (203.05 mg; 0.95 mmol) as a yellow solid (75 mg, 26%—two steps). $^1$H NMR (400 MHz, DMSO-d6): 8.12 (t, J=5.56 Hz, 1H), 6.84 (d, J=8.32 Hz, 2H), 6.50-6.46 (m, 2H), 4.91 (s, 2H), 3.93 (s, 2H), 3.18-3.12 (m, 2H), 2.95 (t, J=4.48 Hz, 2H), 2.52 (s, 2H), 1.73-1.65 (m, 4H), 1.41-1.31 (m, 4H). LC/MS: 330.2 (M+1), 97.2% purity (X-bridge, Maxplot).

Example 8: N-(4-Amino-benzyl)-2-(3,5-dioxo-10-oxa-4-aza-tricyclo[5.2.1.02,6]dec-4-yl)-acetamide

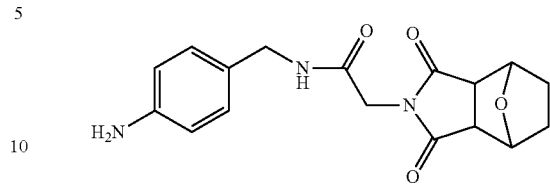

The title compound was prepared following a similar procedure as described for example 4 from 4-Nitro-benzylamine hydrochloride (Alfa, 150 mg, 0.73 mmol) and 3,5-Dioxo-10-oxa-4-aza-tricyclo[5.2.1.02,6]dec-4-yl)-acetic acid (Enamine, 150 mg, 0.66 mmol) as a brown solid (66 mg, 30%—two steps). $^1$H NMR (400 MHz, DMSO-d6) 8.36 (br s, 1H), 6.88 (d, J=7.44 Hz, 2H), 6.49 (d, J=7.60 Hz, 2H), 4.97 (s, 2H), 4.69 (s, 2H), 4.06 (d, J=4.72 Hz, 2H), 3.95 (s, 2H), 3.11 (s, 2H), 1.64 (s, 4H). LC/MS: 330.2 (M+1), 97.8% purity (X-bridge, Maxplot).

Example 9: 2-endo-(3,5-Dioxo-4-aza-tricyclo[5.2.1.02,6]dec-4-yl)-N-[2-(1,2,3,4-tetrahydro-quinolin-6-yl)-ethyl]-acetamide

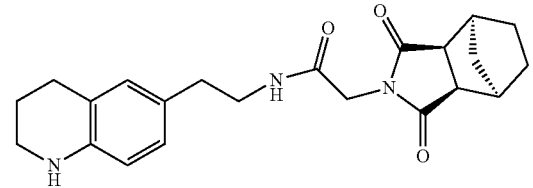 [SMILES: O=C(CN1C(=O)[C@@H]2[C@@H]3CC[C@@H](C3)[C@@H]2C1=O)NCCc1ccc2c(c1)CCCN2]

The title compound was prepared following a similar procedure as described for example 2 from endo-(3,5-Dioxo-4-aza-tricyclo[5.2.1.02,6]dec-4-yl)-acetic acid (Matrix scientific, 150 mg; 0.67 mmol) and 2-(1,2,3,4-Tetrahydro-quinolin-6-yl)-ethylamine dihydrochloride (194 mg; 0.74 mmol) as a yellow solid (10 mg, 38%). 1H NMR (400 MHz, DMSO-d6): 8.14 (t, J=5.56 Hz, 1H), 6.66 (d, J=7.24 Hz, 2H), 6.33 (d, J=8.44 Hz, 1H), 5.43 (s, 1H), 3.91 (s, 2H), 3.13 (t, J=6.20 Hz, 6H), 2.62 (t, J=6.32 Hz, 2H), 2.56 (s, 2H), 2.47 (t, J=7.40 Hz, 2H), 1.78-1.72 (m, 2H), 1.60 (d, J=9.48 Hz, 1H), 1.50 (d, J=9.60 Hz, 1H), 1.43-1.35 (m, 4H). LC/MS: 382.3 (M+1), 99% purity (X-Bridge-Maxplot).

Example 10: N-endo-[2-(4-Amino-phenyl)-ethyl]-2-(3,5-dioxo-4-aza-tricyclo[5.2.1.02,6]dec-4-yl)-acetamide Step 1: Formation of 2-endo-(3,5-Dioxo-4-aza-tricyclo[5.2.1.02,6]dec-4-yl)-N-[2-(4-nitro-phenyl)-ethyl]-acetamide

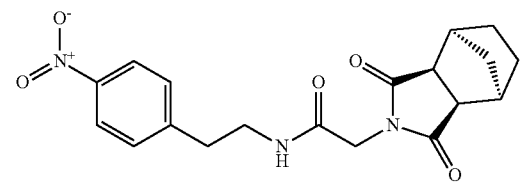 [SMILES: O=C(CN1C(=O)[C@@H]2[C@@H]3CC[C@@H](C3)[C@@H]2C1=O)NCCc1ccc([N+](=O)[O-])cc1]

The title compound was prepared following a similar procedure as described for example 4, step 1 from endo-(3,5-Dioxo-4-aza-tricyclo[5.2.1.0²,⁶]dec-4-yl)-acetic acid (Matrix scientific, 200 mg; 0.90 mmol) and 2-(4-Nitrophenyl)-ethylamine hydrochloride (210 mg; 0.99 mmol) as a yellow solid (130 mg, 39%). 1H NMR (400 MHz, DMSO-d6): 8.23 (t, J=5.52 Hz, 1H), 8.16-8.13 (m, 2H), 7.50 (t, J=1.76 Hz, 2H), 3.90 (s, 2H), 3.34 (t, J=5.92 Hz, 2H), 3.11 (s, 2H), 2.84 (t, J=7.00 Hz, 2H), 2.55 (s, 2H), 1.59 (d, J=9.60 Hz, 1H), 1.49 (d, J=9.64 Hz, 1H), 1.40-1.37 (m, 2H), 1.33-1.23 (m, 2H). LC/MS: 372.0 (M+1), 100% purity (X-Bridge-254 nm).

Step 2: Formation of N-endo-[2-(4-Amino-phenyl)-ethyl]-2-(3,5-dioxo-4-aza-tricyclo[5.2.1.0²,⁶]dec-4-yl)-acetamide

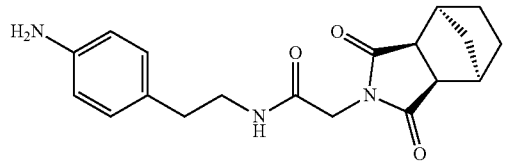 [SMILES: Nc1ccc(CCNC(=O)CN2C(=O)[C@@H]3[C@@H]4CC[C@@H](C4)[C@@H]3C2=O)cc1]

The title compound was prepared following a similar procedure as described for example 4, step 2 from 2-endo-(3,5-Dioxo-4-aza-tricyclo[5.2.1.0²,⁶]dec-4-yl)-N-[2-(4-nitro-phenyl)-ethyl]-acetamide (120 mg; 0.32 mmol) as a yellow solid (80 mg, 70%). 1H NMR (400 MHz, DMSO-d6): 8.14 (s, 1H), 6.84 (d, J=8.32 Hz, 2H), 6.48 (dd, J=6.48, 1.84 Hz, 2H), 4.85 (s, 2H), 3.91 (s, 2H), 3.16-3.11 (m, 4H), 2.56 (s, 2H), 1.59 (s, 1H), 1.50 (d, J=9.60 Hz, 1H), 1.43-1.34 (m, 4H). LC/MS: 342.3 (M+1), 97% purity (X-Bridge-Maxplot).

Example 11: 2-endo-(3,5-Dioxo-4-aza-tricyclo[5.2.1.0²,⁶]dec-4-yl)-N-[1-(2-ethyl-3-oxo-3,4-dihydro-2H-benzo[1,4]oxazin-7-yl)-ethyl]-acetamide

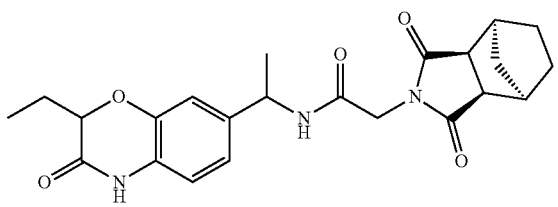 [SMILES: CCC1Oc2cc(C(C)NC(=O)CN3C(=O)[C@@H]4[C@@H]5CC[C@@H](C5)[C@@H]4C3=O)ccc2NC1=O]

The title compound was prepared following a similar procedure as described for example 2 from endo-(3,5-Dioxo-4-aza-tricyclo[5.2.1.0²,⁶]dec-4-yl)-acetic acid (Matrix Scientific, 150 mg; 0.67 mmol) and 7-(1-Amino-ethyl)-2-ethyl-4H-benzo[1,4]oxazin-3-one (165 mg; 0.74 mmol) as a white solid (110 mg, 38%). 1H NMR (400 MHz, DMSO-d6): 10.64 (s, 1H), 8.53 (d, J=6.28 Hz, 1H), 6.90 (d, J=8.24 Hz, 1H), 6.85 (dd, J=8.28, 1.76 Hz, 1H), 6.79 (s, 1H), 4.81-4.74 (m, 1H), 4.47-4.44 (m, 1H), 3.95 (s, 2H), 3.10 (s, 2H), 2.55 (s, 2H), 1.83-1.69 (m, 2H), 1.59 (d, J=9.52 Hz, 1H), 1.49 (d, J=9.60 Hz, 1H), 1.41-1.30 (m, 7H), 0.97 (t, J=7.40 Hz, 3H). LC/MS: 426 (M+1), 98% purity (X-Bridge-254 nm).

Example 12: Biological Assays

CypD Binding Assay:
The binding capacity of the compounds was measured using a competition Fluorescence-Polarisation based assay with fluorescine labelled cyclosporin. The protocol used was adapted from Hausch et al, Med Chem lett 2010, p 536.

CypD Enzymatic Assay:
The peptidyl-proline isomerase activity (PPase) was determined by using a PPase-chymotrypsin coupled assay with suc-AAPF-p-NA as substrated and colorimeric detection adapted from Liu et al., AnalBioChem, 2006 p 100.

SPR Binding:
Binding was confirmed on an SPR surface using a protocol adapted from Mori et al., J. Biomolecular Screening, 2009, p. 419.

The data is interpreted according to the following:

| Compound number | CypD binding ($IC_{50}$) | CypD PPAse ($IC_{50}$) | SPR CypD (KDss) |
|---|---|---|---|
| 1 | A | ND | A |
| 2 | A | A | A |
| 3 | A | ND | A |
| 4 | A | B | A |
| 5 | B | ND | B |
| 6 | B | ND | B |
| 7 | B | ND | B |
| 8 | B | ND | B |
| 9 | B | ND | B |
| 10 | B | ND | B |
| 11 | B | ND | B |

B 10 uM > $IC_{50}$ (or KD) <200 uM
A $IC_{50}$ (or KD) <10 μM
ND Not determined Example 13. Pharmaceutical Preparations (A) Injection vials: A solution of 100 g of an active ingredient according to the invention and 5 g of disodium hydrogen phosphate in 3 l of bidistilled water is adjusted to pH 6.5 using 2 N hydrochloric acid, sterile filtered, transferred into injection vials, is lyophilized under sterile conditions and is sealed under sterile conditions. Each injection vial contains 5 mg of active ingredient.

(B) Suppositories: A mixture of 20 g of an active ingredient according to the invention is melted with 100 g of soy lecithin and 1400 g of cocoa butter, is poured into moulds and is allowed to cool. Each suppository contains 20 mg of active ingredient.

(C) Solution: A solution is prepared from 1 g of an active ingredient according to the invention, 9.38 g of $NaH_2PO_4 \cdot 2H_2O$, 28.48 g of $Na_2HPO_4 \cdot 12H_2O$ and 0.1 g of benzalkonium chloride in 940 ml of bidistilled water. The pH is adjusted to 6.8, and the solution is made up to 1 l and sterilized by irradiation. This solution could be used in the form of eye drops.

(D) Ointment: 500 mg of an active ingredient according to the invention is mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

(F) Coated tablets: Tablets are pressed analogously to Example E and subsequently are coated in a conventional manner with a coating of sucrose, potato starch, talc, tragacanth and dye.

(G) Capsules: 2 kg of an active ingredient according to the invention are introduced into hard gelatin capsules in a conventional manner in such a way that each capsule contains 20 mg of the active ingredient.

(H) Ampoules: A solution of 1 kg of an active ingredient according to the invention in 60 l of bidistilled water is sterile filtered, transferred into ampoules, is lyophilized under sterile conditions and is sealed under sterile conditions. Each ampoule contains 10 mg of active ingredient.

(I) Inhalation spray: 14 g of an active ingredient according to the invention are dissolved in 10 l of isotonic NaCl solution, and the solution is transferred into commercially available spray containers with a pump mechanism. The solution could be sprayed into the mouth or nose. One spray shot (about 0.1 ml) corresponds to a dose of about 0.14 mg.

While a number of embodiments of this invention are described herein, it is apparent that the basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula I,

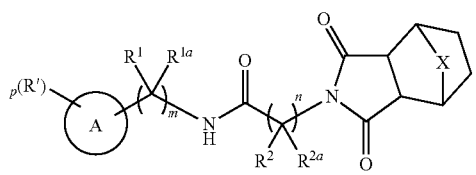

or a pharmaceutically acceptable salt thereof, wherein:
Ring A is

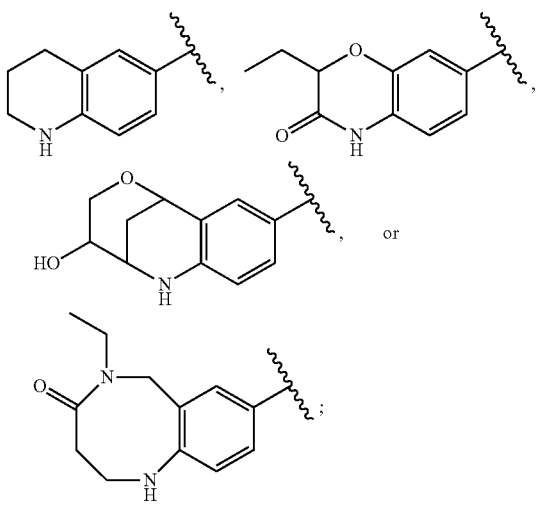

each R' is independently —R, halogen, -haloalkyl, -hydroxyalkyl, —OR, —C(O)R, —$CO_2$R, —C(O)N(R)$_2$, —NRC(O)R, or —N(R)$_2$;
each $R^1$ is independently —H or $C_{1-6}$ aliphatic which is optionally substituted;
each $R^{1a}$ is independently —H or $C_{1-6}$ aliphatic which is optionally substituted;

or $R^1$ and $R^{1a}$ taken together with the atom to which they are attached form a 3-7 membered carbocyclic ring optionally having 1-4 heteroatoms independently selected from nitrogen, oxygen, or sulfur, which is optionally substituted;
each $R^2$ is independently —H or $C_{1-6}$ aliphatic which is optionally substituted;
each $R^{2a}$ is independently —H or $C_{1-6}$ aliphatic which is optionally substituted;
X is $CH_2$; or X and the bonds attached to X are absent;
each R is independently hydrogen, $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or
two R groups on the same atom are taken together with the atom to which they are attached to form a $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
m is 1 or 2;
n is 1 or 2; and
p is 1, 2, 3, 4, or 5.

2. The compound of claim 1, wherein each R' is independently —R, —OR, or —N(R)$_2$.

3. The compound of claim 2, wherein each R' is independently H, -Me, -Et, —OH, or —NH$_2$.

4. The compound of claim 1, wherein X is CH$_2$.

5. The compound of claim 1, wherein X, and the bonds attached to X, are absent.

6. The compound of claim 1, wherein each $R^1$ is independently —H or -Me.

7. The compound of claim 1, wherein $R^1$ and $R^{1a}$ taken together with the atom to which they are attached form a cyclopropyl, cyclobutyl, cyclopentyl, or cyclohexyl, each of which is optionally substituted.

8. The compound of claim 1, of formula II:

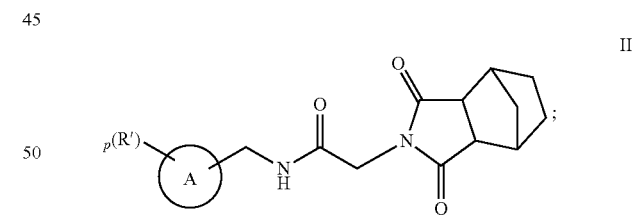

or a pharmaceutically acceptable salt thereof.

9. The compound of claim 1, of formula V:

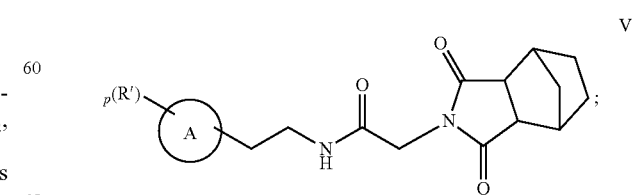

or a pharmaceutically acceptable salt thereof.

10. The compound of claim 1, of formula VI:

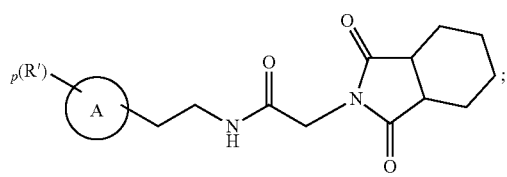

or a pharmaceutically acceptable salt thereof.

11. A compound selected from:

1
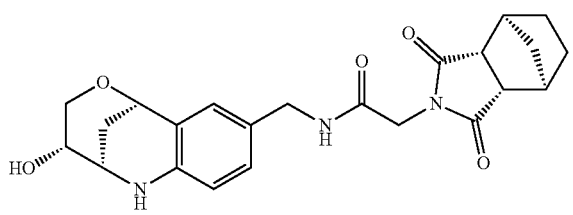

2
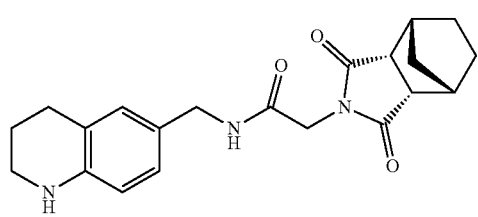

3
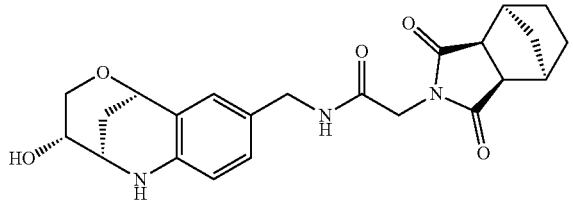

4
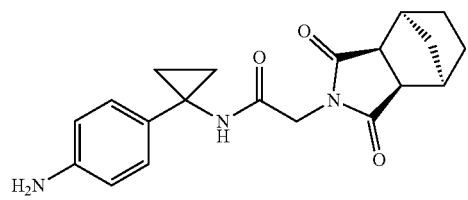

5
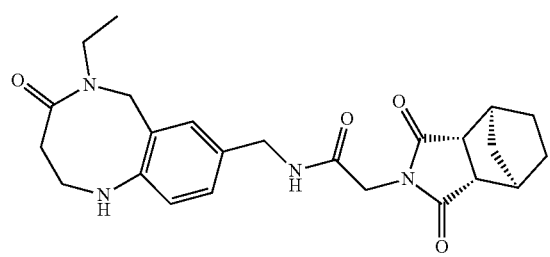

6
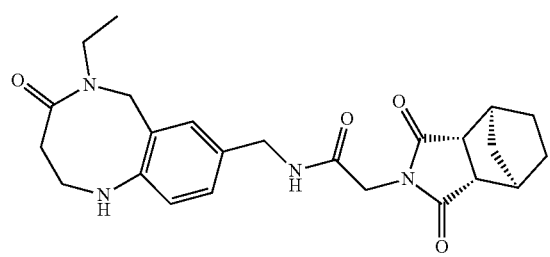

-continued

8
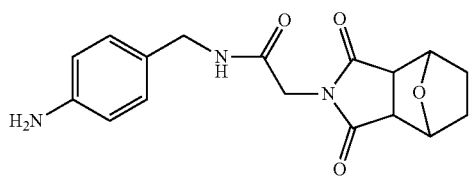

9
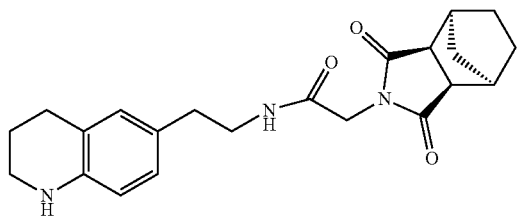

10
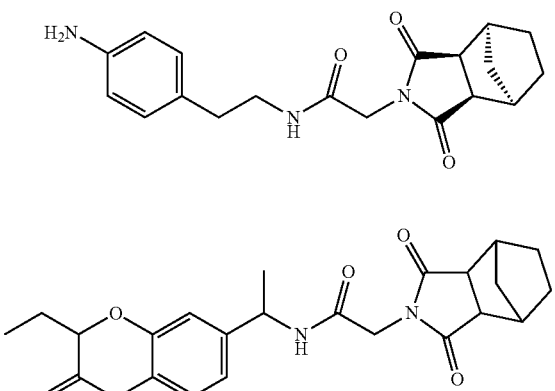

11
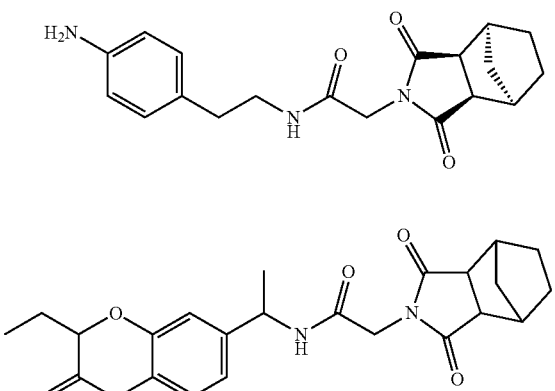

12. A pharmaceutical composition comprising a compound of claim 1, and a pharmaceutically acceptable adjuvant, carrier, or vehicle.

13. The compound of claim 1, wherein each $R^1$ is independently —H, -Me, or -Et.

14. The compound of claim 1, wherein $R^1$ and $R^{1a}$ taken together with the atom to which they are attached form a cyclopropyl, cyclobutyl, cyclopentyl, or cyclohexyl.

15. A compound

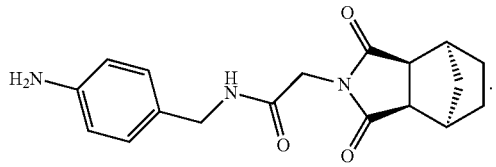 [SMILES: Nc1ccc(CNC(=O)CN2C(=O)[C@@H]3[C@@H]4CC[C@@H](C4)[C@@H]3C2=O)cc1]

\* \* \* \* \*